United States Patent [19]

Audia et al.

[11] Patent Number: 5,300,645
[45] Date of Patent: Apr. 5, 1994

[54] TETRAHYDRO-PYRIDO-INDOLE

[75] Inventors: James E. Audia; James J. Droste, both of Indianapolis, Ind.; Deborah A. Evrard, Cambridge, Mass.

[73] Assignee: Eli Lilly and Company, Indianapolis, Ind.

[21] Appl. No.: 48,392

[22] Filed: Apr. 14, 1993

[51] Int. Cl.⁵ ............................................. C07D 471/04
[52] U.S. Cl. ........................................ 546/49; 546/56; 546/70; 546/85; 546/86; 546/87
[58] Field of Search ................... 546/49, 56, 70, 85, 546/86, 87

[56] References Cited

PUBLICATIONS

Chem. Abstracts, 81(15):91397w, vol. 81, p. 453 (1974).
Chem. Abstracts, 90(1):6594b, vol. 90 p. 806 (1979).
Chem. Abstracts, 77(25):164922t, vol. 77, p. 440 (1972).
Hudlicky et al., J. Org. Chem., 46, 1738-1741 (1981).
Meyers et al., J. Org. Chem., 47, 2229-2231 (1982).
Chem. Abstracts, 109:93404s, vol. 109, p. 751 (1988).
Afsah et al., Monatsh. Chem., 116(6-7), pp. 851-855 (1985).
Sandrin et al., J. Org. Chem. 54(23), 5636-5640.
Beilstein 292199, RN 114999-79-0, citing Provita et al., Collect. Czech. Chem. Commun., 24 74, 77, 80 (1959).

Primary Examiner—C. Warren Ivy
Assistant Examiner—Phyllis G. Spivack
Attorney, Agent, or Firm—MaCharri R. Vorndran-Jones; Leroy Whitaker

[57] ABSTRACT

The present invention provides a new Pictet-Spengler process useful for preparing tetrahydro-beta-carboline compounds.

6 Claims, No Drawings

TETRAHYDRO-PYRIDO-INDOLE

FIELD OF THE INVENTION

The present invention relates to the field of organic chemistry. The invention provides novel tetrahydro-beta carboline compounds with a high affinity for the 5-HT$_{1c}$ receptor.

BACKGROUND OF THE INVENTION

A substantial body of evidence supports the relationship between 5-HT$_{1c}$ receptor modulation and a variety of diseases and conditions.

The 5-HT$_{1c}$ receptor subtype was first detected in choroid plexus epithelial cells and is the only 5HT receptor subtype expressed by these cells. Studies of the 5-HT$_{1c}$ receptor using radioligand binding have been complex due to the cross reactivity of the 5-HT$_{1c}$ receptor with the 5-HT$_{1c}$ receptor. The discovery of selective, high affinity compounds which discriminate between 5-HT$_{1c}$ and 5-HT$_2$ has been an elusive and important target. Hartig et al., The 5-HT$_{1c}$ Receptor *Annals New York Academy of Science* 149, 159. Compounds with selective affinity for the 5-HT$_{1c}$ receptor can provide treatment for 5-HT$_{1c}$-receptor-mediated conditions without the side effects associated with activity at the 5-HT$_2$ receptor. Such compounds can simplify characterization of the 5-HT$_{1c}$ receptor and provide useful new therapeutic agents. In vitro, m-chlorophenylpiperazine (m-CPP) has a slightly higher affinity for the 5-HT$_{1c}$ sites than for other 5-HT receptors; however, prior to the present invention, there have been no known 5-HT$_{1c}$ selective ligands.

The activation of the 5-HT$_{1c}$ receptor has been associated with numerous behavioural and physiological effects. *TiPS* 11, 181 (May 1990). The 5HT$_{1c}$ receptors in the limbic system can affect mood, behavior, and hallucinogenesis. Hartig et al., *The* 5-HT$_{1c}$ *Receptor Annals New York Academy of Science* 149, 159. Modulation of the 5HT$_{1c}$ receptors has been associated with schizophrenia and schizophreniform disorders. Ugedo, L. et. al. *Psychopharmacology*, 98, 45 (1989); Canton H. et. al. *Eur. J. Pharmacol.* 191, 93 (1990). Hypothalamic 5-HT$_{1c}$ receptors can influence sleep, appetite, thermoregulation, sexual behavior, motor activity, and neuroendocrine function. Hartig et al., The 5-HT$_{1c}$ Receptor *Annals New York Academy of Science* 149, 159. Additionally, studies indicate that 5-HT$_{1c}$ receptors mediate hypoactivity, caused decreased feeding in rats, and have anxiogenic effects. Id. Studies have shown that drug-induced penile erections are 5-HT$_{1c}$ mediated. *Psychopharmacology* 101, 57 (1990). Likewise, 5-HT$_{1c}$ modulation can treat or prevent priapism.

Other studies have used m CPP to characterize responses associated with 5-HT$_{1c}$ receptors. Although responses to 5-HT$_{1c}$ are difficult to characterize by this method, the studies evince that 5-HT$_{1c}$ receptors influence the onset of anxiety, obsessive-compulsive disorders, panic disorders, Gilles de la Tourette syndrome and migraine headaches. *TiPS* 11, 181 (May 1990). The studies indicate that the 5-HT$_{1c}$ receptor can be involved in Alzheimer's disease as well. Id. The 5-HT$_{1c}$ receptor is involved in the modulation of the balance of cerebrospinal fluid. Further, the 5-HT$_{1c}$ receptor is associated with the sensation of pain. Zemlan, F. P. et al. *Neurochem. Int.* 16, 507 (1990).

It would be advantageous to have compounds which would permit modulation of the 5-HT$_{1c}$ receptor. It would be particularly desirable to have compounds with high 5-HT$_{1c}$ receptor affinity and low 5-HT$_{1c}$ receptor affinity. It would be further advantageous to have compounds that minimize the effects of eating disorders, sexual disorders, and other disorders or conditions associated with 5-HT$_{1c}$ modulation.

SUMMARY OF THE INVENTION

This invention provides a group of novel compounds with 5-HT$_{1c}$ receptor activity. The invention also provides compounds with the longed for selective 5-HT$_{1c}$ receptor antagonist activity. Additionally, the present compounds are useful tools to characterize the effects of the 5-HT$_{1c}$ receptor and to develop therapeutic agents based on 5-HT$_{1c}$ receptor modulation.

Further, the present invention provides a new method for preparing compounds with 5-HT$_{1c}$ receptor activity.

This invention relates to a compound of the formula (I)

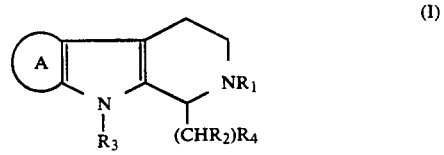

wherein:
R$_1$ is hydrogen or C$_1$–C$_3$ alkyl;
R$_2$ is hydrogen or C$_1$–C$_6$ alkyl;
R$_3$ is hydrogen or C$_1$–C$_3$ alkyl;
R$_4$ is bicyclic or substituted bicyclic;
A is selected form the group consisting of

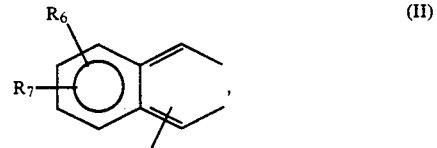

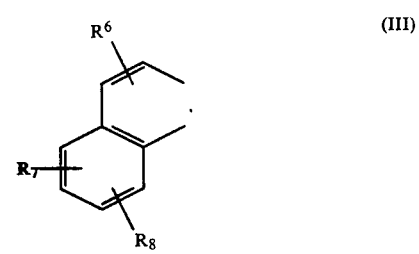

and

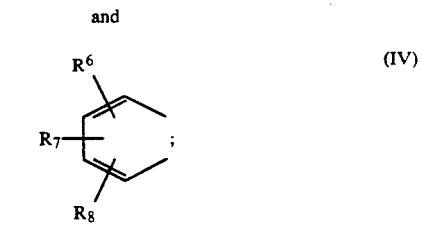

wherein
R$_6$ and R$_7$ are, independently, hydrogen, C$_1$–C$_6$ alkyl, C$_2$–C$_6$ alkenyl, halo, halo (C$_1$–C$_6$)alkyl, halo(C$_1$–C$_6$)alkenyl, COR$_5$, C$_1$–C$_{10}$ alkanoyl, CO$_2$R$_5$, (C$_1$–C$_6$)$_m$ alkylamino, NO$_2$, —SR$_5$, or OR$_5$;

m is 1 or 2;

$R_5$ is independently hydrogen or $C_1-C_4$ alkyl;

$R_{5'}$ is $C_1-C_4$ alkyl;

$R_8$ is independently selected from the group consisting of an $R_6$ group, substituted $C_3-C_8$ cycloalkyl, $C_3-C_8$ cycloalkyl, $C_3-C_8$ cycloalkyl-($C_1-C_1$)alkyl, $C_5-C_8$ cycloalkenyl, substituted $C_5-C_8$ cycloalkenyl, $C_5-C_8$ cycloalkenyl-($C_1-C_1$)alkyl, $C_7-C_{16}$ arylalkyl; or $R_6$ and $R_7$ together with the carbon atoms of group A form a 5- to 8-member carbon ring; or a pharmaceutically acceptable salt or solvate thereof.

The present invention also provides methods of employing, and pharmaceutical formulations containing, a compound of formula (I) or a pharmaceutically acceptable salt or solvate thereof.

This invention provides a new process for preparing a compound of formula (VI)

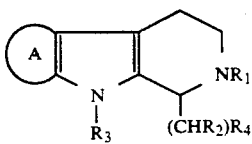

(VI)

wherein $R_2$ is hydrogen and $R_1$, $R_3$, $R_4$, $R_5$, $R_6$, $R_7$, $R_8$, and A are as defined supra;

or a pharmaceutically acceptable salt or solvate thereof;

which process comprises contacting a compound of the formula (VII)

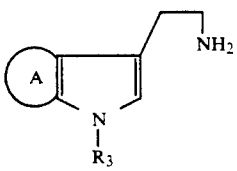

(VII)

with a lactone of formula (VIII)

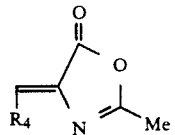

(VIII)

in the presence of a protic acid.

DETAILED DESCRIPTION OF THE INVENTION

The term "treating" as used herein includes prophylaxis of the named physical and/or mental condition or amelioration or elimination of the developed physical and/or mental condition once it has been established.

The phrase "injury to the central nervous system" includes, but is not limited to, injury to the spinal cord, neural tube, or dura of the brain. Injury to the central nervous system also includes priapism, cerebrospinal fluid imbalances, and other 5-$HT_{1c}$ imbalances, and related conditions resulting from central nervous system injury.

The terms "$C_1-C_n$ alkyl" wherein n=2-10, as used herein, represent a branched or linear alkyl group having from one to the specified number of carbon atoms. Typical $C_1-C_6$ alkyl groups include methyl, ethyl, n-propyl, iso-propyl, butyl, iso-butyl, sec-butyl, tert-butyl, pentyl, hexyl and the like.

The terms "$C_2-C_n$ alkenyl" wherein n=3-10, as used herein, represents an olefinically unsaturated branched or linear group having from 2 to 10 carbon atoms and at least one double bond. The groups can be branched or straight chain. Examples of such groups include 1-propenyl, 2-propenyl (—$CH_2$—CH=$CH_2$), 1-butenyl (—CH=$CHCH_2CH_3$), 1,3-butadienyl (—CH=CHCH=$CH_2$), hexenyl, pentenyl, and the like.

The terms "halide", "halogen", and "halo" include fluorine, chlorine, bromine, and iodine. The preferred halogen is chlorine.

The terms "halo($C_1-C_6$)alkyl" and "halo($C_2-C_6$)alkenyl" refer to alkyl or alkenyl substituents having one or more independently selected halo atoms attached at one or more available carbon atoms. These terms include chloromethyl, bromoethyl, trifluoroethyl, trifluoromethyl, trifluoroethylenyl, 3-bromopropyl, 3-bromopropenyl, 2-bromopropyl, 2-bromopropenyl, 3-chlorobutyl, 3-chlorobutenyl, 3,2-dichlorobutyl, chloroethylenyl, fluoropentenyl, 3-chloro-2-bromohexenyl, 3-chloro-2-bromobutyl, trichloromethyl, dichloroethyl, 1,4-dichlorobutyl, 3-bromopentyl, 1,3-dichlorobutyl, 1,1-dichloropropyl, and the like. More preferred halo-($C_1-C_6$)alkyl groups are trichloromethyl, trichloroethyl, and trifluoromethyl. The most preferred halo-($C_1-C_6$)alkyl is trifluoromethyl.

The term "$C_1-C_{10}$ alkanoyl" represents a group of the formula C(O)($C_1-C_9$) alkyl. Typical $C_1-C_{10}$ alkanoyl groups include acetyl, propanoyl, butanoyl, and the like.

The term "($C_1-C_6$ alkyl)$_m$amino" wherein m=1-2; refers to either a mono- or a dialkylamino group in which the alkyl portion of the group may be straight or branched. Examples of such groups are dimethylamino, diethylamino, methylamino, ethylamino, 2-propylamino, 1-propylamino, di(n-propyl)amino, di(isopropyl)amino, methyl-n-propylamino, t-butylamino, and the like.

The term "$C_3-C_n$ cycloalkyl" wherein n=4-8, represents cyclopropyl, cyclobutyl, cyclopentyl, cyclohexyl, cycloheptyl, and cyclooctyl.

The term "substituted($C_5-C_n$) cycloalkyl" refers to a cycloalkyl group as described supra wherein the cycloalkyl group may be substituted with from one to four substituents independently selected from the group consisting of hydrogen, $C_1-C_6$ alkyl, $C_3-C_8$ cycloalkyl, $NO_2$, halo, halo($C_1-C_6$)alkyl, halo($C_2-C_6$)alkenyl, $C_2-C_6$ alkenyl, $C_3-C_8$ cycloalkyl-($C_1-C_3$)alkyl, $C_5-C_8$ cycloalkenyl, $C_5-C_8$ cycloalkenyl-($C_1-C_3$)alkyl, $COR_5$, $C_1-C_{10}$ alkanoyl, $C_7-C_{16}$ arylalkyl, $CO_2R_5$, ($C_1-C_6$ alkyl)$_m$amino, —$SR_5$, and $OR_5$.

The term "$C_3-C_8$ cycloalkyl-($C_1-C_3$)alkyl" represents a linear alkyl group substituted at a terminal carbon with a $C_3-C_8$ cycloalkyl group. Typical cycloalkylalkyl groups include cyclohexylethyl, cyclohexylmethyl, 3-cyclopentylpropyl, and the like.

The term "$C_5-C_8$ cycloalkenyl" represents an olefinically unsaturated ring having five to eight carbon atoms, e.g., cyclohexadienyl, cyclohexenyl, cyclopentenyl, cycloheptenyl, cyclooctenyl, cyclohexadienyl, cycloheptadienyl, cyclooctatrienyl and the like. The cycloalkenyl group may be substituted with from one to four substituents selected from the group consisting of hydrogen, $C_1-C_6$ alkyl, $NO_2$, halo, halo($C_1-C_6$)alkyl, halo($C_2-C_6$)alkenyl, $C_2-C_6$ alkenyl, ($C_1-C_6$ alkyl)-

$_m$amino, COR$_5$, C$_1$-C$_{10}$ alkanoyl, OR$_5$, CO$_2$R$_5$, —SR$_5$, and C$_7$-C$_{16}$ arylalkyl.

The term "C$_5$-C$_8$ cycloalkenyl-(C$_1$-C$_3$)alkyl" represents a linear C$_1$-C$_3$ alkyl group substituted at a terminal carbon with a C$_5$-C$_8$ alkenyl group.

The term "aryl" represents phenyl or naphthyl. The aryl group can be unsubstituted or can have one or two substituents independently selected from the group consisting of C$_1$-C$_6$ alkyl, C$_3$-C$_8$ cycloalkyl, C$_3$-C$_6$ alkenyl, C$_3$-C$_8$ cycloalkyl-(C$_1$-C$_3$)alkyl, (C$_1$-C$_6$ alkyl)-$_m$amino, phenyl, C$_5$-C$_8$ cycloalkenyl, C$_5$-C$_8$ cycloalkenyl-(C$_1$-C$_3$)alkyl, COR$_5$, C$_1$-C$_{10}$ alkanoyl, OR$_5$, and C$_7$-C$_{16}$ arylalkyl. The substituents may be located at any available position on the aryl ring.

The term "C$_7$-C$_{16}$ arylalkyl" represents an aryl-(C$_1$-C$_{10}$)alkyl substituent wherein the alkyl group is linear, such as benzyl, phenethyl, 3 phenylpropyl, or phenyl-t-butyl; or branched.

The term "bicyclic" represents either an unsaturated or saturated stable fused or bridged 7- to 12-membered bicyclic carbon ring. The bicyclic ring may be attached at any carbon atom which affords a stable structure. The bicyclic structure is illustrated by the formula

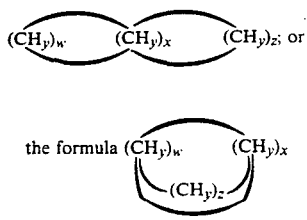

wherein y is independently 1 or 2; w, x, and z are independently 1 to 5; (w+z) is greater than 2; and bonds may be present as necessary to afford a stable structure with the desired degree of saturation. The term includes, but is not limited to, naphthyl, tetralinyl, decalinyl, compounds of the formula

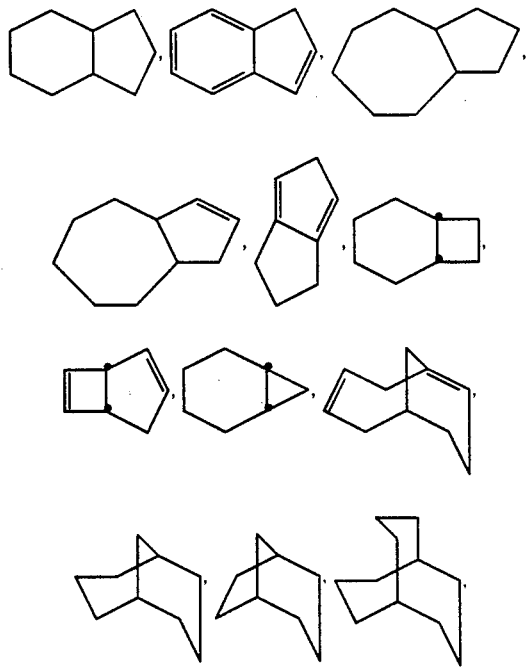

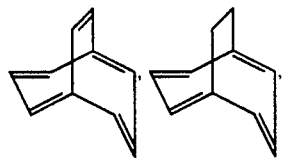

and the like. It is understood that the exemplatory structures do not limit the scope of the invention in any way.

The term "substituted bicyclic" refers to a bicyclic ring system with from one to four substituents attached at any desired positions on the bicyclic ring system. The bicyclic substituents may be independently selected from the group consisting of hydrogen, C$_1$-C$_6$ alkyl, NO$_2$, halo, halo(C$_1$-C$_6$)alkyl, halo(C$_2$-C$_6$)alkenyl, C$_2$-C$_6$ alkenyl, COR$_5$, C$_1$-C$_{10}$ alkanoyl, C$_7$-C$_{16}$ arylalkyl, CO$_2$R$_5$, (C$_1$-C$_6$ alkyl)$_m$amino, —SR$_5$, and OR$_5$; wherein m and R$_5$ are defined supra. It is intended that the substituted bicyclic substituent may bond to the CHR$_2$ group through any available carbon atom in the bicyclic ring system. The term includes, but is not limited to compounds such as, 2-methyltetralinyl, 3-hydroxytetralinyl, 4-nitrotetralinyl, 3-dimethylaminonaphthyl, 2-methoxynaphthyl, 6-chlorodecalinyl, 8-ethenylnaphthyl, and the like.

The term "naphthyl" refers to a naphthalene ring system substituent, as commonly used in organic chemistry. The naphthyl substituent may bond to the CHR$_2$ group through any available carbon atom in the naphthyl ring system. The term "substituted naphthyl" refers to a naphthyl ring system with from one to four sustituents attached at any desired positions on the naphthyl ring system. The naphthyl substituents may be independently selected from the "substituted bicyclic" group supra.

The term "phenyl" as used herein refers to an unsubstituted benzene ring system. The term "substituted phenyl" refers to a benzene ring system with from one to three substituents independently selected from the group of bicyclic substituents defined supra.

The term "organic solvent" includes solvents containing carbon, such as halogenated hydrocarbons, ether, toluene, xylene, benzene, and tetrahydrofuran.

The term "agitate" includes such techniques as stirring, centrifugation, mixing, and other similar methods.

The term "aprotic solvent" refers to polar solvents of moderately high dielectric constant which do not contain an acidic hydrogen. Examples of common aprotic solvents are dimethyl sulfoxide (DMSO), dimethylformamide, sulfolane, tetrahydrofuran, ether, methyl-t-butyl ether, or 1,2-dimethoxyethane.

The term "protic solvent" refers to a solvent containing hydrogen that is attached to oxygen, and hence is appreciably acidic. Common protic solvents include such solvents as water, methanol, ethanol, 2-propanol, and 1-butanol.

The term "inert atmosphere" refers to reaction conditions in which the mixture is covered with a layer of inert gas such as nitrogen or argon.

The term "protic acid" refers to an acid having an acidic hydrogen. Preferred protic acids include hydrochloric acid, formic acid, perchloric acid, sulfuric acid, and phosphoric acid in an aqueous medium. The most preferred protic acids are hydrochloric acid, sulfuric acid, and formic acid.

The term "selective binding of a 5-HT$_{1c}$ receptor" refers to a method of binding the 5-HT$_{1c}$ receptor to a greater extent than it binds the 5-HT$_2$ receptor.

The term "substantially pure" is intended to mean at least about 90 mole percent, more preferably at least about 95 mole percent, and most preferably at least about 98 mole percent of the desired enantiomer or stereoisomer is present compared to other possible configurations.

The term "ligand" refers to compounds that are by the 5-HT$_{1c}$ receptor. Compounds useful as 5-HT$_{1c}$ selective ligands may be used to selectively occupy the 5-HT$_{1c}$ receptor site or may act as a selective agonist at the 5-HT$_{1c}$ receptor site.

The abbreviations used herein have their accepted meaning, unless stated otherwise. For example, "Me" and "Et" refer to methyl, ethyl respectively, and "t-Bu" refers to tertiary-butyl. The abbreviation "RT" refers to room temperature or ambient conditions unless indicated otherwise.

The abbreviation "TMEDA" refers to tetramethylethylenediamine. "THF" refers to tetrahydrofuran. "MOMCl" refers to chloromethylmethyl ether. "Ph" refers to a phenyl group The terms "MeO" and "EtO" refer to methoxy and ethoxy substituents which are bound to the parent molecule through the oxygen.

The formula (I) compounds can form acid addition salts with a wide variety of inorganic and organic acids. Typical acids which can be used include sulfuric, hydrochloric, hydrobromic, phosphoric, hypophosphoric, hydroiodic, sulfamic, citric, acetic, maleic, malic, succinic, tartaric, cinnamic, benzoic, ascorbic, mandelic, p-toluenesulfonic, benzenesulfonic, methanesulfonic, trifluoroacetic, hippuric and the like. The pharmaceutically acceptable acid addition salts of the formula (I) are especially preferred.

The compounds of the present invention are useful for modulating or blocking the 5-HT$_{1c}$ receptor. Certain of the present compounds are preferred for that use. Preferred compounds are those having the following characteristics:

A) R$_1$ is hydrogen;
B) R$_2$ is hydrogen or methyl;
C) R$_3$ is hydrogen or methyl;
D) R$_4$ is naphthyl or substituted naphthyl wherein the naphthyl substituents are selected from the group consisting of (C$_1$-C$_6$ alkyl)$_m$amino and OR$_5$;
E) A is a group of formula III;
F) A is a group of formula IV wherein R$_6$ and R$_7$ are independently selected from the group consisting of hydrogen, C$_1$-C$_5$ alkyl, and halo. R$_8$ is independently selected from the group consisting of hydrogen, C$_1$-C$_5$ alkyl, halo, C$_5$-C$_8$ cycloalkyl, phenyl and substituted-phenyl;
G) R$_2$ is hydrogen;
H) R$_3$ is hydrogen;
I) R$_4$ is naphthyl, or substituted naphthyl wherein the substituents are selected from dialkylamino and OR$_5$;
J) A is a group of formula IV wherein R$_6$ is hydrogen, R$_7$ is hydrogen or methyl, and R$_8$ is C$_1$-C$_4$ alkyl, Br, or F.

The more preferred classes of compounds have the following features:
A-C, E or F and I.
The most preferred class has the following features:
A and G-J.

The preferred classes of compounds for use as selective 5-HT$_{1c}$ ligands have the following features:
A-D and E or J.
The most preferred class of compounds for use as selective 5-HT$_{1c}$ ligands has the following features:
A and G-J.

The Formula (I) compounds have useful central nervous system activity. Table I illustrates several of the Formula (I) compounds. The terms in the column headings of Table I refer to Formula (I). As used in the table, the headings "S$_1$", "S$_2$", and "S$_3$" refer to the substituents on the R$_4$ group.

(I)

[Structure of Formula I showing bicyclic A ring fused to pyridine with N-R$_3$, NR$_1$, and (CHR$_2$)R$_4$ substituents]

The abbreviations for the R$_4$ group refer to the following:

[Structures of R$_4$A, R$_4$B, R$_4$C, R$_4$D, R$_4$E, R$_4$F, R$_4$G, R$_4$H, R$_4$I, R$_4$J, R$_4$K, R$_4$L showing various bicyclic and tricyclic ring systems with S$_1$, S$_2$, S$_3$ substituents]

-continued

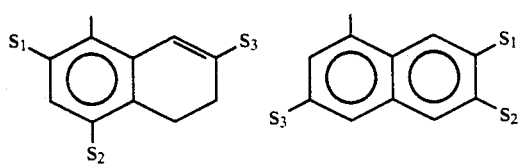

R4M    R4N

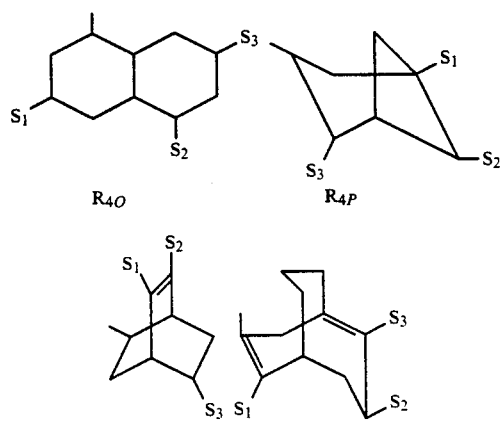

R4O    R4P

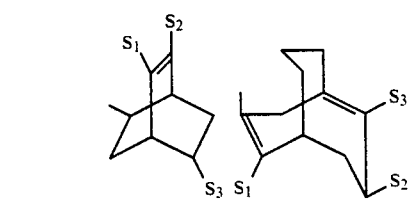

R4Q    R4R

-continued

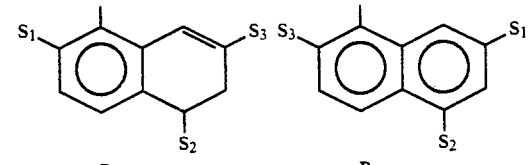

R4S    R4T

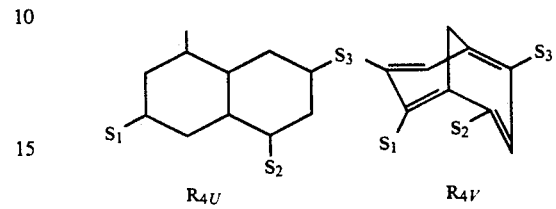

R4U    R4V

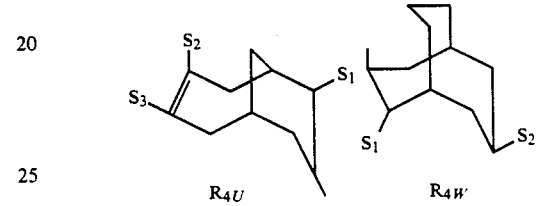

R4U    R4W

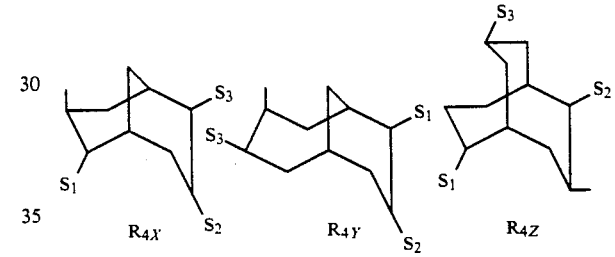

R4X    R4Y    R4Z

TABLE I

| A | $R_1$ | $R_2$ | $R_3$ | $R_4$ | $S_1$ | $S_2$ | $S_3$ | $R_6$ | $R_7$ | $R_8$ |
|---|---|---|---|---|---|---|---|---|---|---|
| II | H | H | H | $R_{4A}$ | OH | t-Bu | H | NHPr | H | H |
| III | Me | Me | Me | $R_{4B}$ | OMe | OMe | H | Me | Me | H |
| IV | Et | Et | Et | $R_{4C}$ | $NMe_2$ | H | H | $C_2H_3$ | H | Cl |
| IV | H | $C_6H_{13}$ | Pr | $R_{4D}$ | $NBu_2$ | H | H | H | $C_3H_5$ | Br |
| III | Me | $C_5H_{11}$ | H | $R_{4E}$ | $NPr_2$ | H | H | H | H | H |
| IV | Et | $C_4H_9$ | Me | $R_{4F}$ | $NEt_2$ | H | H | H | H | H |
| III | H | $C_3H_7$ | Et | $R_{4G}$ | NHMe | H | H | H | H | $C_4H_7$ |
| II | Me | $C_3H_5$ | Pr | $R_{4H}$ | NHBu | H | NHMe | H | H | H |
| III | Et | Pr | H | $R_{4I}$ | NHPr | H | H | H | H | H |
| IV | Pr | Bu | Me | $R_{4J}$ | NHEt | H | $NMe_2$ | Et | H | Me |
| II | H | H | Et | $R_{4K}$ | $CH_2Cl$ | H | H | $C_2H_3$ | Cl | F |
| III | Pr | Me | H | $R_{4L}$ | H | Br | H | OH | $C_3H_5$ | H |
| IV | Et | Et | Me | $R_{4M}$ | OH | OMe | F | H | H | Ph |
| II | Pr | H | Et | $R_{4N}$ | $NO_2$ | H | H | OH | OMe | H |
| III | Me | Me | H | $R_{4O}$ | H | Cl | Me | Pr | Me | F |
| IV | H | H | H | $R_{4P}$ | OMe | H | H | H | OMe | OMe |
| III | Me | Me | Me | $R_{4Q}$ | H | OMe | H | Me | H | H |
| II | Et | Et | Et | $R_{4R}$ | H | H | OMe | OBu | F | H |
| IV | Pr | Pr | Pr | $R_{4S}$ | H | OMe | H | OEt | Cl | H |
| III | H | Bu | H | $R_{4T}$ | H | H | OH | Me | H | H |
| II | Me | H | Me | $R_{4U}$ | H | OH | H | Me | H | Br |
| IV | Et | Me | Et | $R_{4V}$ | F | Cl | H | H | H | H |
| III | Pr | H | Pr | $R_{4X}$ | Cl | OMe | OMe | Cl | $NMe_2$ | $NO_2$ |
| II | H | Me | Pr | $R_{4Y}$ | Br | Me | OMe | Me | Et | H |
| IV | Me | Et | Et | $R_{4Z}$ | $CO_2C_2H_5$ | H | H | $COC_2H_5$ | H | Me |
| III | Et | Pr | Me | $R_{4D}$ | OMe | OMe | OMe | H | H | H |
| IV | Pr | Bu | H | $R_{4E}$ | H | H | H | Me | F | F |
| III | H | $C_5H_{11}$ | Me | $R_{4F}$ | OMe | OMe | OMe | $NMe_2$ | H | Cl |
| IV | Me | $C_6H_{13}$ | Me | $R_{4G}$ | F | OEt | H | $C_2H_4Cl$ | H | F |
| III | Et | H | H | $R_{4H}$ | Cl | OH | Br | OEt | OMe | OH |
| IV | H | H | Pr | $R_{4I}$ | $NO_2$ | OMe | OMe | H | Me | H |
| II | Et | Me | H | $R_{4J}$ | Cl | OH | Br | H | Et | OMe |
| III | Me | Et | H | $R_{4K}$ | Cl | OMe | OH | Et | H | H |
| IV | Et | H | Et | $R_{4L}$ | H | H | SH | $C_2H_3$ | Cl | H |

TABLE I-continued

| A | $R_1$ | $R_2$ | $R_3$ | $R_4$ | $S_1$ | $S_2$ | $S_3$ | $R_6$ | $R_7$ | $R_8$ |
|---|---|---|---|---|---|---|---|---|---|---|
| III | Pr | Me | H | $R_{4M}$ | H | F | NHBu | H | H | $C_4H_7$ |
| IV | H | H | Pr | $R_{4N}$ | COMe | H | H | OH | OMe | H |
| II | Me | Bu | H | $R_{4O}$ | OMe | $NMe_2$ | H | H | H | Ph |
| IV | Et | H | Me | $R_{4P}$ | OEt | $NMe_2$ | OMe | $NO_2$ | t-Bu | H |
| III | H | Me | H | $R_{4Q}$ | H | H | $NO_2$ | Pr | Me | H |
| III | Me | Et | Me | $R_{4R}$ | H | F | H | F | Me | F |
| II | Et | Pr | H | $R_{4S}$ | $CO_2H$ | H | H | H | H | $C_3H_5$ |
| IV | H | Bu | H | $R_{4T}$ | Br | Cl | H | Et | H | Me |
| III | Me | $C_4H_9$ | H | $R_{4U}$ | H | OMe | Cl | Cl | Me | Cl |
| II | Et | H | Pr | $R_{4V}$ | H | F | OH | H | H | H |
| IV | H | Me | Me | $R_{4W}$ | Cl | OMe | H | H | H | H |

The present invention contemplates racemic mixtures as well as the substantially pure stereoisomers of the compounds of Formula I. The term "enantiomer" is used herein as commonly used in organic chemistry to denote a compound which rotates the plane of polarization. Thus, the "—enantiomer" rotates the plane of polarized light to the left, and contemplates the levorotary compound of Formula I. The + and —enantiomers can be isolated using classical resolution techniques. One particularly useful reference Which describes such methods is JACQUES et. al. ENANTIOMERS, RACEMATES, AND RESOLUTIONS (John Wiley and Sons 1981). Appropriate resolution methods include direct crystallization, entrainment, and crystallization by optically active solvents. Chrisey, L. A. *Heterocycles*, 267, 30 (1990). A preferred resolution method is crystallization with an optically active acid or by chiral synthesis as described in Example 46 using the method of A. I. Meyers. Loewe, M. F. et al., *Tetrahedron Letters*, 3291, 26 (1985), Meyers, A. I. et al., *J. Am. Chem. Soc.* 4778, 110 (1988). Preferred optically active acids include camphorsulfonic and derivatives of tartaric acid.

For example the invention includes, but is not limited to compounds such as (—)-(S)-6-methyl-1-[(4-dimethylamino-naphthalenyl)-methyl]-1,2,3,4-tetrahydro-9H-pyrido[3,4-b]indole, (—)-(S)-6-methyl-1-(1-naphthalenyl-1-ethyl)-1,2,3,4-tetrahydro-9H-pyrido[3,4-b]indole, (—)-(S)-6-(1,1-dimethylethyl)-1-(1-naphthalenyl-1-ethyl)-1,2,3,4-tetrahydro-9H-pyrido[3,4-b]indole, and (—)-(S)-6-(1,1-dimethylethyl)-1,2,3,4-tetrahydro-1-(1-naphthalenylmethyl)-9H-pyrido[3,4b]indole. The invention also includes, but is not limited to, (+)-(S)-6-methyl-1-[( 4-dimethylamino-naphthalenyl)-methyl]-1,2,3,4-tetrahydro-9H pyrido[3,4-b]indole, (+)-(S)-6 methyl-1-(1-naphthalenyl-1-ethyl)-1,2,3,4-tetrahydro-9H-pyrido[3,4-b]indole, (+)-(S)-6-(1,1-dimethylethyl)-1-(1-naphthalenyl-1-ethyl)-1,2,3,4-tetrahydro-9H-pyrido[3,4-b]indole, and (+)-(S)-6-(1,1-dimethylethyl)-1,2,3,4-tetrahydro-1-(1-naphthalenylmethyl)-9H-pyrido[3,4b]indole.

The compounds of the present invention are known to form hydrates and solvates with appropriate solvents. Preferred solvents for the preparation of solvate forms include water, alcohols, tetrahydrofuran, DMF, and DMSO. Preferred alcohols are methanol and ethanol. Other appropriate solvents may be selected based on the size of the solvent molecule. Small solvent molecules are preferred to facilitate the corresponding solvate formation. The solvate or hydrate is typically formed in the course of recrystallization or in the course of salt formation. One useful reference concerning solvates is Sykes, Peter, *A Guidebook to Mechanism in Organic Chemistry*, 56+, 6th Ed (1986, John Wiley & Sons, New York). As used herein, the term "solvate" includes hydrate forms, such as monohydrates and dihydrates.

The compounds of the present invention can be prepared using chemical processes that are understood in the art; however, the most preferred method for preparing the formula (I) compounds of this invention utilizes a novel process which is illustrated in Scheme V. The process of Scheme V is a Pictet-Spengler type reaction.

Traditionally, the Pictet-Spengler reaction consists of the condensation of a β-arylethylamine with a carbonyl compound to yield a tetrahydroisoquinoline. Pictet et. al. 44 *Ber.* 2030 (1911). The Pictet-Spengler reaction has been extended to the condensation of substituted amines and tryptamines with various aldehydes. Decker et. al. 395 *Ann.* 342 (1913). Unfortunately, the known Pictet-Spengler reaction often requires drastic reaction conditions, results in undesired by-products, and the effectiveness of the reaction is closely related o the carbonyl compound used in the reaction. Shono et. al. 48 *J. Org. Chem.* 1621–1628 (1983). The traditional Pictet-Spengler carbonyl compounds are acetaldehyde derivatives which may be tedious to prepare and isolate. Often the overall yield using the traditional Pictet-Spengler reaction is undesirably low. The new process of this invention utilizes naphthaldehydes which are simple to prepare.

This Pictet-Spengler type reaction is generally applicable, provides desirable yields, and produces stable intermediates. Further, the product of the reaction typically may be directly isolated as the desired salt.

Surprisingly, Applicants have discovered that compounds of formula I, wherein $R_2$ is hydrogen, may be prepared by contacting a lactone compound of formula (i) with an amine of formula (h) in the presence of a protic acid. This Pictet-Spengler type reaction is generally applicable, provides desirable yields, and produces stable intermediates. Further, the product of the reaction typically may be directly isolated as the desired salt.

The compounds of formula (a) which may be used as starting materials for the compounds of the instant invention can be purchased from art-recognized vendors or may be prepared using well-known chemical techniques. Furniss, Brian S. et al., *Vogel's Textbook of Practical Organic Chemistry*, 989–993, 5th Ed. (1989, John Wiley & Sons, New York). The compounds of formula (b) which are useful as starting materials for the compounds of this invention may be prepared as represented by Scheme I. The $R_4$ group is as defined herein above.

The process for preparing the compounds of this invention will be discussed in greater detail in the following paragraphs.

Scheme I

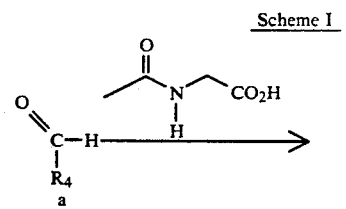

Compound (a) in Scheme I may be Substituted or unsubstituted depending on the desired product. Most formula (a) compounds necessary for the preparation of the azalactone (b) starting materials are commercially available. Additional substituted formula (a) compounds may prepared using common chemical methods. Furniss, Brian S. et al., *Vogel's Textbook of Practical Organic Chemistry*, 989-993, 5th Ed. (1989, John Wiley & Sons, New York).

Generally, the Scheme I reaction is begun by preparing a solution of compound (a), acetylglycine and sodium acetate in acetic anhydride. The reaction is commonly heated from about 90° C. to about 110° C. for a period of about 2-15 hours. The reaction mixture is cooled to about ambient temperature and stirred for a period of about 0-10 hours under inert conditions. The reaction time will vary depending on the degree of substitution on the bicyclic ring and the completion of reaction desired.

When the reaction is complete, the mixture is poured onto ice with stirring. The azalactone (b) may be isolated by standard isolation techniques such as filtration and may be dried under reduced pressure.

Compound (d) in Scheme II is used as a starting material for compounds of formula (I). These compounds are commercially available or may be prepared using a modification of the well-known Fischer indole synthesis for the synthesis of tryptamines. The modified Fischer synthesis is represented by Scheme II. "A" is as hereinabove defined.

Scheme II

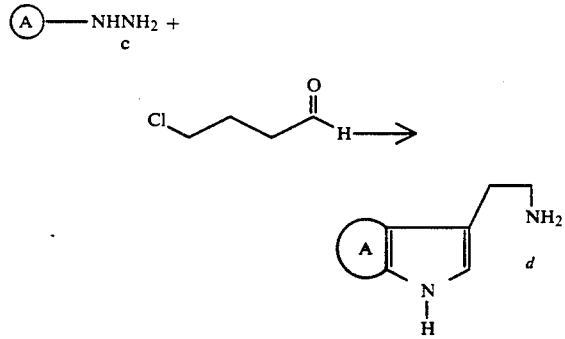

The chlorobutanal compound used in Scheme II may be prepared through the hydrogenation of chlorobutyryl chloride. Other halobutanal compounds may be suitable for the Scheme II hydrogenation. The hydrogenation may be facilitated by the use of a catalyst such as Pd/C. The starting compounds (c) in Scheme II may be purchased or prepared using known methods. March, Jerry, *Advanced Organic Chemistry*, 1163, 3rd (1985, John Wiley & Sons, New York).

The modified Fischer synthesis is commonly begun by adding a suitable saturated base like sodium carbonate to a stirred suspension of the hydrazine salt in an organic solvent like chloroform. The hydrazine hydrochloride salt is one especially preferred hydrazine salt. The desired hydrazine free base is extracted with the organic phase. The oil is placed in an alcohol and water solution and treated with an appropriate base like sodium acetate. The halobutanal is added and the tube purged with an inert gas like nitrogen. The resulting mixture is placed in an oil bath which has been heated to about 90°C.-110° C. The mixture should be heated for about 17 to 19 hours. The mixture is allowed to cool to ambient temperature and is concentrated under reduced pressure. The residue is partitioned between a suitable organic and basic aqueous phase, such as chloroform/methanol and aqueous sodium carbonate. The organic phase may be concentrated and the resulting compound (d) purified by standard methods such as flash chromatography. If chromatography is used, fractions containing product may be combined and concentrated. The oil is dissolved in an appropriate solvent, such as diethyl ether containing about 1% alcohol. A preferred alcohol is methanol. The mixture may be treated with dry acid gas, such as dry HCl gas to produce the corresponding acid addition salt of the desired compound (d).

One method for preparing Formula (I) compounds uses the Pictet-Spengler reaction as represented by Scheme III. The substituents are as defined hereinabove.

Scheme III

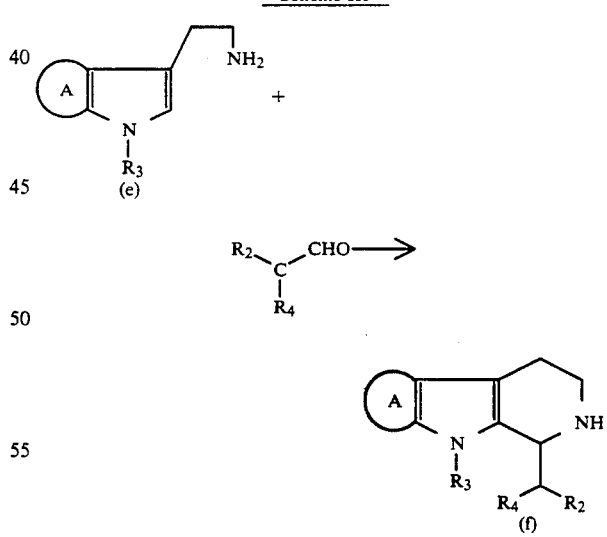

Generally, the Scheme III reaction is carried out by refluxing compound (e) with the selected aldehyde in a suitable solvent such as ethanol or methanol for a period of about 35 to 50 hours. The precipitated reaction product (f) is collected by common isolation methods, such as filtration and may be purified by recrystallization. If a compound with an $R_1$ substituent is desired, the reaction may be followed by a reductive alkylation. The reductive alkylation is represented by Scheme IV.

Scheme IV

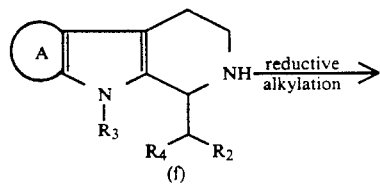
(f)

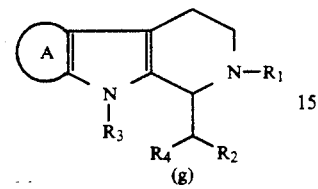
(g)

A protic acid and aldehyde solution is commonly added to an aqueous solution of compound (f). The most preferred protic acid is formic acid. The most preferred aldehyde is formaldehyde. The artisan can readily choose other appropriate reagents for the reductive alkylation. The resulting solution is refluxed for a period of about 4 to 80 hours. After reflux the solution should be made basic using an appropriate base such as potassium carbonate. The desired product can then be extracted with an appropriate organic phase, such as chloroform. The product can be dried, concentrated, and purified by known methods such as flash chromatography.

A preferred method for preparing Formula (I) compounds, wherein $R_2$ is hydrogen, utilizes a new modified Pictet-Spengler reaction, described supra, as represented by Scheme V. The substituents are as defined hereinabove.

Scheme V

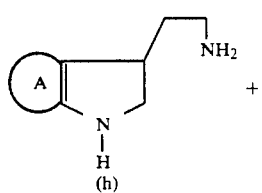
(h)

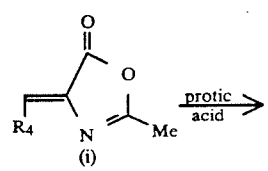
(i)

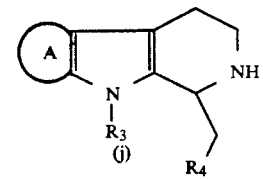
(j)

Compound (h) and compound (i) are contacted in a suitable protic aqueous acid solution under inert conditions. Most preferably, compound (h) and compound (i) are refluxed under inert conditions for a period of about 20 to about 30 hours. Preferred protic acids include formic acid and hydrochloric acid. The most preferred acid solution is 1 N HCl. If direct isolation is not effective, then the reaction mixture may be neutralized with an appropriate base, such as potassium carbonate, followed by extraction with an organic phase, such as chloroform. The product can be isolated through solvent removal followed by chromatographic isolation, such as silica gel chromatography, or other common isolation techniques. Typically the product is isolated as the acid addition salt. Appropriate salt forms are discussed supra.

As noted above, the compounds of the present invention can exist as resolved enantiomers. The single (−)enantiomer may be prepared by the method of A. I. Meyers as represented by Scheme VI infra. The (+)enantiomer may be prepared using known resolution techniques described supra. All substituents are as defined hereinabove.

Scheme VI

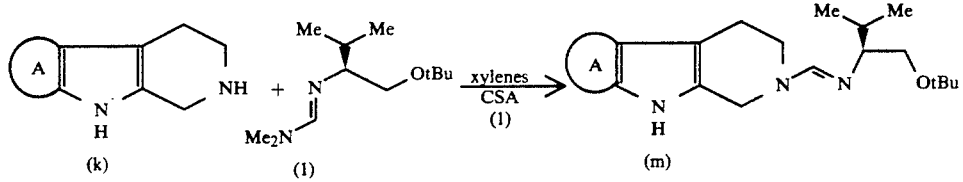

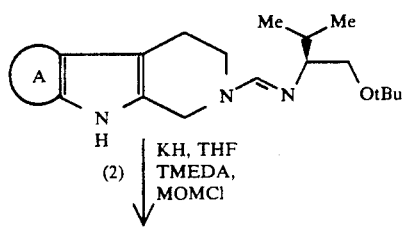

-continued
Scheme VI

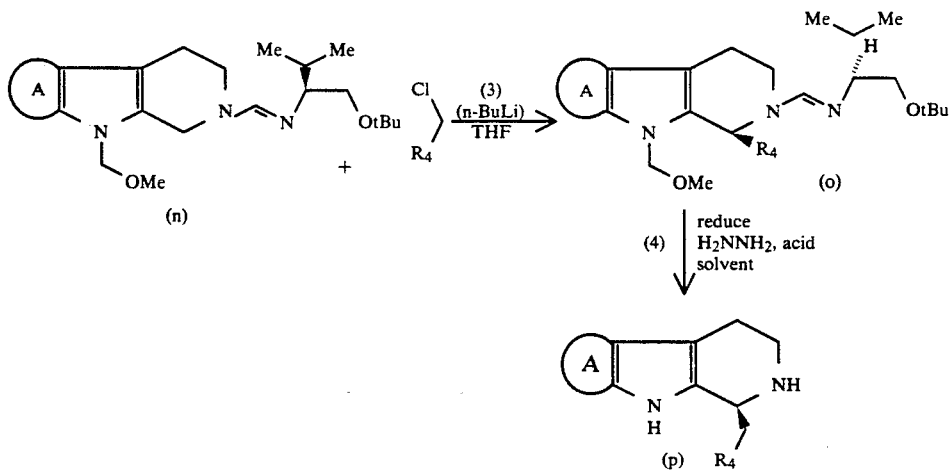

In Scheme VI, CSA represents camphorsulfonic acid. Butylformadine (1) is prepared from the amino acid valine using known methods. Other formadine compounds will also work. In step 1, the compound (k) and butylformadine (1) solution is refluxed for a period of about 70 to 80 hours. The product of the reflux reaction can be purified by standard isolation methods, such as flash chromatography. The isolated oil can be used without further purification.

Compound (m) prepared in step 1, can be added to a suspension of potassium hydride (KH) in tetrahydrofuran (THF). Tetramethylethylenediamine (TMEDA), and then chloromethylmethyl ether (MOMCl) are added to the solution, as represented by step 2. The mixture is stirred for a period of about 1 hour. The mixture can be treated with water and partitioned between an appropriate organic, such as diethyl ether, and water. The product should be extracted with the organic phase, dried over potassium carbonate, and concentrated. The resulting oil may be used in subsequent steps without further purification.

In step 3, n-BuLi is slowly added dropwise to a stirred, cooled (about $-76°$ C. to $-80°$ C.) solution of the formadine in dry THF. The solution is stirred for a period of about 1 hour followed by addition of the chloro compound in dry THF. The solution is stirred for an additional period of about 4-5 hours at the reduced temperature. The mixture is allowed to cool to room temperature for a period of about 4 to 14 hours. Wet THF is added and the solution concentrated. The residue is dissolved in an appropriate organic solvent such as chloroform and washed with water. The organic phase is dried over a suitable drying agent, such as sodium carbonate, and concentrated to facilitate purification of the desired product. The product may be isolated by flash chromatography and concentrated. The resulting oil may be used in subsequent steps without further purification.

The deprotection reaction represented in step 4 is begun at reduced temperature (about 0° C). Water, acetic acid, and hydrazine hydrate are added to compound (o). The reaction temperature is decreased to about $-10°$ C. to $-20°$ C. for a period of about 60-120 hours. The mixture is allowed to warm to ambient temperature and is concentrated. The product is dissolved in an appropriate organic phase, such as chloroform, and washed with water. The organic phase is dried over a suitable drying agent, such as sodium carbonate, and concentrated to a viscous oil. The oil is dissolved in an appropriate solvent, such as diethyl ether and treated with a suitable organic or inorganic acid to afford the desired acid addition salt. The salt can be isolated and purified by common chemical methods.

If the desired product has an alkyl group at the $R_3$ position, the reaction represented by Scheme VII may be employed.

Scheme VII
(Step a)

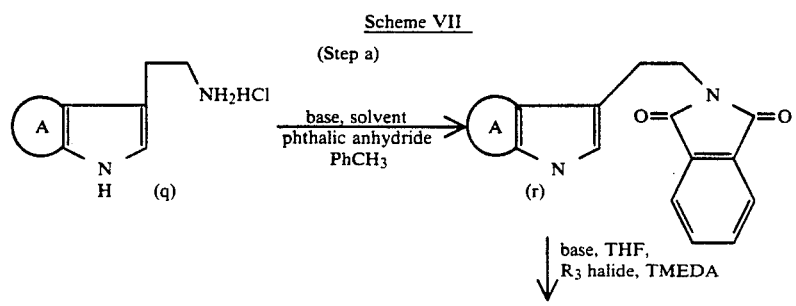

Scheme VII

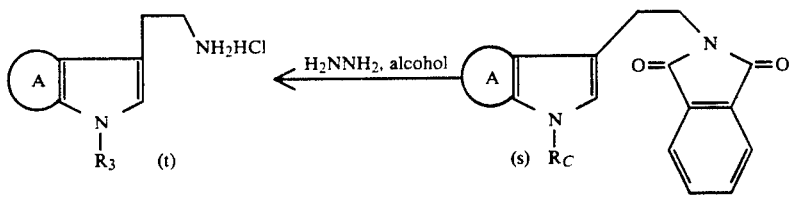

In Scheme VII, an appropriate saturated base solution, such as sodium carbonate, is added to compound (q). The desired compound (q) salt may be prepared by the method of Scheme II, above. The mixture is stirred at about ambient temperature for a period of about 1 hour. The layers are separated, and the aqueous layer is extracted with an appropriate organic solvent, such as chloroform. The organic layers are dried over an appropriate drying agent, such as sodium sulfate, and concentrated. The residue is dissolved in a suitable solvent such as toluene and treated with phthalic anhydride. The solution is refluxed for a period of about 12 to 20 hours with azeotropic drying. The solution is cooled, concentrated, and recrystallized to give compound (r).

Compound (r) is mixed in THF. A cooled (about 0° C.) suspension of an appropriate base, such as potassium hydride in dry THF, is slowly added to the compound (r) solution. After the addition of the the base, the mixture is stirred for a period of about 1 hour. Tetramethylethylenediamine (TMEDA) is added, followed by a haloalkyl such as methyl iodide (MeI). After about 1 hour, the reaction is quenched by the addition of water, followed by extraction with an appropriate organic phase, such as diethyl ether. The organic phases are dried over an appropriate drying agent, such as magnesium sulfate and concentrated.

A solution of the concentrated compound (s) (above) is contacted with an appropriate solvent, such as methanol, and treated with hydrazine. The mixture is refluxed for a period of about 2 hours. The mixture is cooled to ambient temperature and treated with concentrated acid, such as HCl. The mixture is then treated with an alcohol and refluxed for a period of about 12 to 20 hours. Preferred alcohols include methanol, ethanol, and butanol. After cooling to ambient temperature, the mixture is partitioned between a suitable organic and an aqueous phase. One suitable combination is chloroform and concentrated sodium carbonate solution. The aqueous layer may be further extracted, the organic phases combined, dried, and concentrated. The product may be purified by flash chromatography, concentrated, and converted to a desired salt. The resulting compound (t) may be used in Scheme III or Scheme V to produce the desired Formula (I) compounds.

The following Examples further illustrate certain of the compounds of the present invention, and methods for their preparation. The examples are illustrative only, and are not intended to limit the scope of the invention.

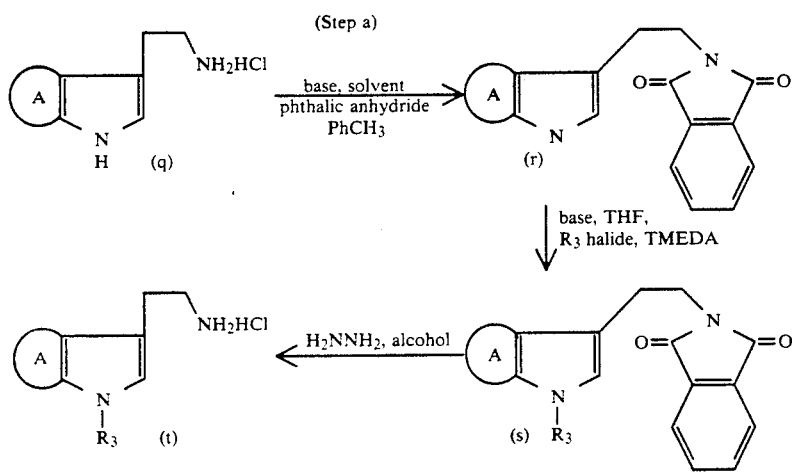

(Step a)

The column chromatography procedures used standard flash chromatography techniques. One well-known reference describing appropriate flash chromatography techniques is Still, W. C. Kahn, and Mitra, *J. Org. Chem.* 1978, 43, 2932. Fractions containing product were generally evaporated under reduced vacuum to provide the product.

Optical rotations were obtained using methanol, pyridine, or other suitable solvent.

The hydrochloride salt of the particular compound was prepared by placing the free base into diethyl ether containing an alcohol such as methanol, or other suitable solvent mixture. While stirring this ether solution, a solution of HCl in diethyl ether was added dropwise until the solution became acidic. Alternatively, the ether solution was treated with dry HCl gas.

The maleate salt of the particular compound was prepared by placing the free base in ethyl acetate or other suitable solvent and treating with maleic acid. The precipitate formed was filtered and dried to provide the corresponding maleate salt of the free base.

EXAMPLE 1

Preparation of (+/−)
6-methyl-1-(1-(4-methoxynaphthalenyl)methyl)-1,2,3,4-tetrahydro-9H-pyrido[3,4-b]-indole hyrochloride

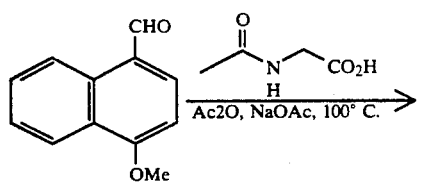

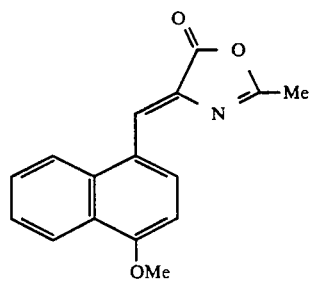

A solution of 4-methoxy-1-naphthaldehyde (20.0 g, 0.107 mol), N-acetylglycine (12.58 g, 0.107 mol) and sodium acetate (8.81 g, 0.107 mol) in acetic anhydride (100 mL) was heated to 100° C. for 2 hours. The reaction mixture was cooled to ambient temperature and stirred for 10 hours under nitrogen atmosphere. The mixture was poured onto ice (250 mL) with stirring. The product was isolated by filtration, washed with water (3×50 mL) and diethyl ether (3×50 mL) and dried under reduced pressure (3.16 g ).

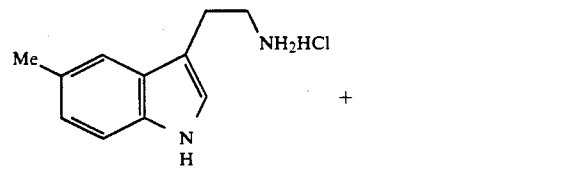

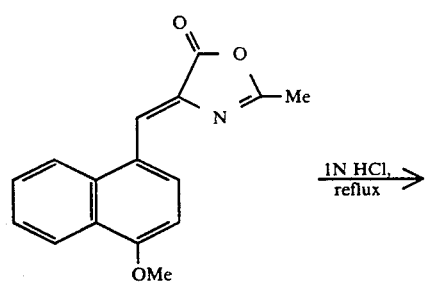

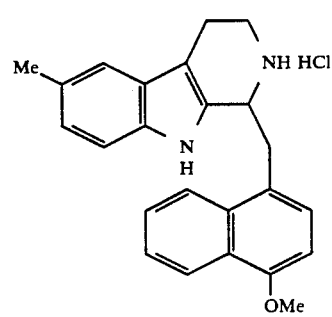

A suspension of azalactone prepared above (2.00 g, 7.5 mmol) and 5-methyltryptamine hydrochloride (1.18 g, 5.62 mmol) in 1N HCl (20 mL) was heated to reflux for 48 hours under nitrogen atmosphere. The reaction mixture was cooled to ambient temperature and the crude product isolated by filtration. The brown solid was triturated with isopropyl alcohol (3×50 mL) and washed with diethyl ether (3×50 mL). Recrystallization from ethanol afforded 1.42 g of desired product as a pale solid.

(mp 271.7° C.).

| Analysis: | Calculated | Found |
|---|---|---|
| C | 73.36 | 73.60 |
| H | 6.41 | 6.51 |
| N | 7.13 | 7.20 |

EXAMPLE 2

Preparation of (+/−)
6-methyl-1-(1-(2-methoxynaphthalenyl)methyl)1,2,3,4-tetrahydro-9H-pyrido[3,4-b]-indole hydrochloride

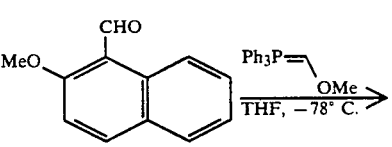

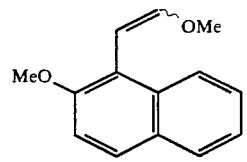

To a stirred, cooled (−78° C.) solution of methoxymethyl-triphenylphosphonium chloride (11.05 g, 32.2 mmol) in 150 mL of anhydrous THF was added n-butyllithium (20.14 mL of 1.6 M solution in hexanes, 32.2 mmol) dropwise via syringe. After complete addition, the solution was stirred at this temperature for 15 min. A solution of 2-methoxy-1-naphthaldehyde (5.0 g, 26.9 mmol) in THF (75 mL) was added to the solution dropwise by addition funnel. After complete addition, the solution was allowed to warm to ambient temperature and stir for 14 hours. A saturated solution of ammonium chloride (100 mL) was added and the mixture was partitioned between diethyl ether and water. The organic phase was dried over anhydrous sodium sulfate, filtered and concentrated under reduced pressure. The crude residue was purified by plug filtration (silica gel, eluent 40% ethyl acetate/hexanes) and afforded 5.0 g of product as a mixture of enol ethers, which was used without further purification.

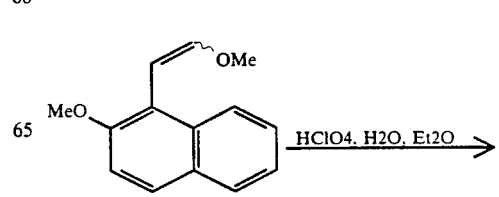

-continued

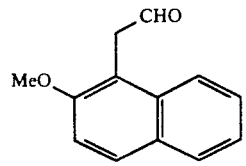

A solution of enol ethers prepared above (5.0 g, 23.3 mmol) in diethyl ether (50 mL) was treated with water (1.0 mL) and perchloric acid (1.5 mL of 60% solution). The solution was stirred at ambient temperature for 72 hours. The solution was diluted with chloroform (100 mL) and neutralized with saturated sodium bicarbonate solution. The mixture was extracted with chloroform (3×100 mL) and the combined organic phases were dried over sodium sulfate and concentrated. The residue was purified by flash chromatography on silica gel (5% diethyl ether/hexanes as eluent) to afford (2-methoxy-1-naphthyl)-acetaldehyde (1.79 g) as a colorless oil.

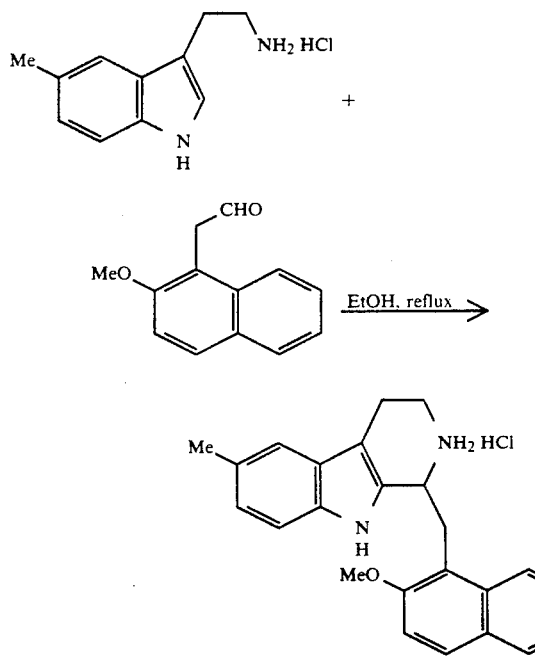

To a stirred solution of 5-methyltryptamine hydrochloride (947 mg, 4.49 mmol) in 20 mL of ethyl alcohol was added (2-methoxy-1-naphthyl)-acetaldehyde (1.0, 4.99 mmol). The solution was heated to reflux under nitrogen atmosphere for 40 hours. The reaction mixture was cooled to ambient temperature and the crude product isolated by filtration. Recrystallization from ethyl alcohol/2-butanone afforded product as a pale solid (705 mg).
(mp. 245.3° C.).

| Analysis: | Calculated | Found |
|---|---|---|
| C | 73.36 | 73.29 |
| H | 6.41 | 6.64 |
| N | 7.13 | 7.12 |

EXAMPLE 3

Preparation of (+/−) 6-methyl-1-(1-naphthalenyl-1-ethyl)-1,2,3,4-tetrahydro-9H-pyrido[3,4-b]indole

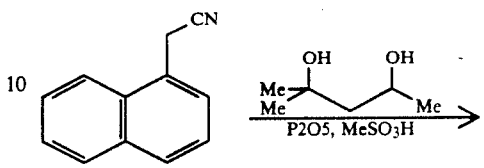

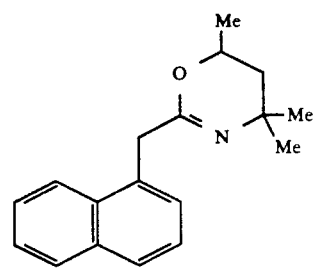

To methanesulfonic acid (215 mL) was added phosphorus pentoxide (31.8 g) slowly with stirring. After the addition was complete, the mixture was further stirred under nitrogen atmosphere for 2 hours until homogeneous. To this solution was added 1-naphthylacetonitrile (50 g, 0.3 mol) in a single portion, followed by 2-methyl-2,4-pentanediol (76.4 mL, 0.6 mol) dropwise at such a rate as to maintain a temperature between 25° and 30° C. (1 hour). After complete addition, the reaction mixture was stirred at ambient temperature for 10 hours and poured onto ice (500 g). The mixture was made basic with sodium hydroxide solution (50%), added at such a rate as to keep the temperature below 35° C. The mixture was extracted with diethyl ether (3×250 mL) and the combined organic phases were dried over magnesium sulfate and concentrated under reduced pressure to afford a green solid.

Recrystallization from ethyl acetate afforded intermediate product (28.3 g) which was used without further purification.

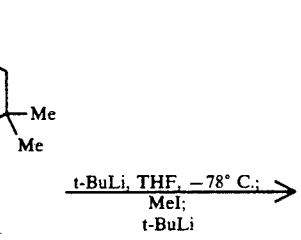

t-BuLi, THF, −78° C.;
MeI;
t-BuLi

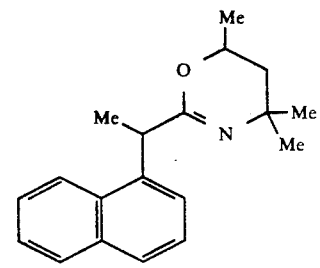

To a cooled (−78° C.) solution of previously prepared intermediate product (28.3 g, 0.106 mol) in THF (475 mL) under argon atmosphere was added t-butyllithium solution (68.4 mL, 1.7M in pentane, 0.116 mol) dropwise via syringe with stirring over 15 minutes. After complete addition, the orange solution was stirred at −78° C. for 30 minutes. Methyl iodide (6.6 mL, 0.106 mol) was added dropwise via syringe and the resulting solution further stirred at −78° C. for 45 minutes. t-Butyllithium (68.4 mL, 1.7M in pentane, 0.116 mol) was added dropwise over 15 minutes and the orange solution stirred for 2 hours. The mixture was poured into ice/water (500 mL) and was acidified to pH 2-3 with 5N HCl solution. The mixture was extracted with diethyl ether (2×100 mL) and these extracts were discarded. The aqueous phase was made basic with sodium hydroxide solution (50%), cooling the mixture with ice when necessary. The basic aqueous phase was extracted with diethyl ether (2×200 mL) and the combined organic extracts were dried over magnesium sulfate, filtered and concentrated to afford product as an oily solid (13.15 g), which was used without further purification.

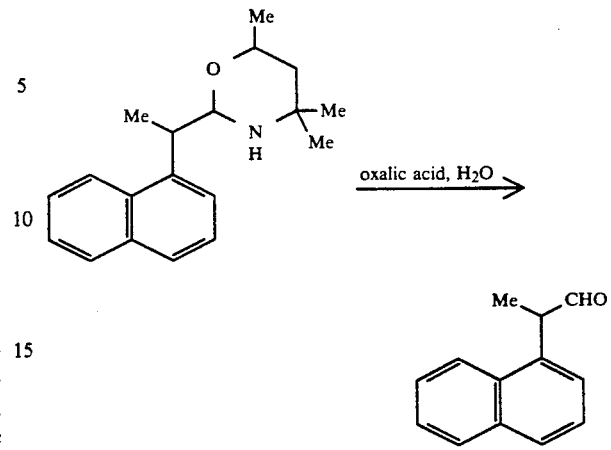

A mixture of crude product from the previous reaction (13.2 g, 46.6 mmol) and oxalic acid dihydrate (19.1 g, 152 mmol) in water (380 mL) was heated to reflux for 12 hours. The mixture was cooled to ambient temperature and extracted with chloroform (2×100 mL). The combined organic phases were dried over magnesium sulfate, filtered and concentrated to afford aldehyde as an orange oil. Distillation (Kugelrohr) under reduced pressure afforded pure aldehyde (1.97 g) as a pale oil.

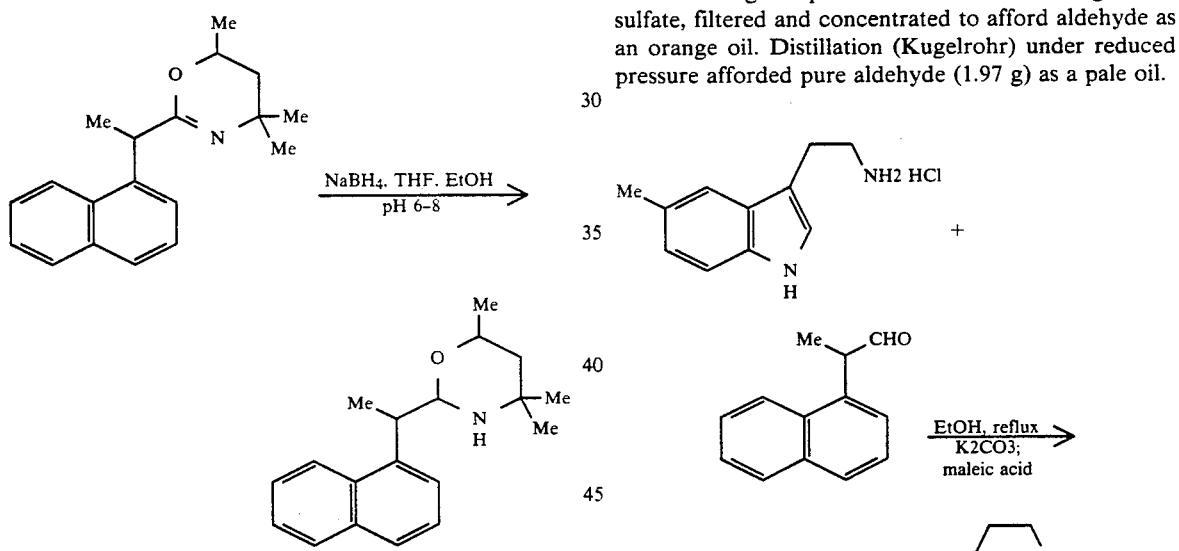

To a stirred cooled (−40° C.) solution of previous product (13.15 g, 46.7 mmol) in THF (100 mL) and ethyl alcohol (100 mL) was added 5N HCl solution until pH 7. In a separate flask, a solution of sodium borohydride (2.52 g, 65.8 mmol) was dissolved in water (20 mL) to which 1 drop of 50% sodium hydroxide had been added. Portions of the sodium borohydride solution and 5N HCl solution were alternately added to the reaction mixture such that the pH remained 6-8, at such a rate as to maintain temperature between −35° and −45° C. After complete addition, the reaction mixture was warmed to ambient temperature over about 2 hours. The reaction mixture was made basic with sodium hydroxide solution and extracted with diethyl ether (3×100 mL). The combined organic phases were washed with brine and dried over magnesium sulfate. Filtration and removal of solvent afforded crude product (13.2 g) as a viscous oil, which was used without further purification.

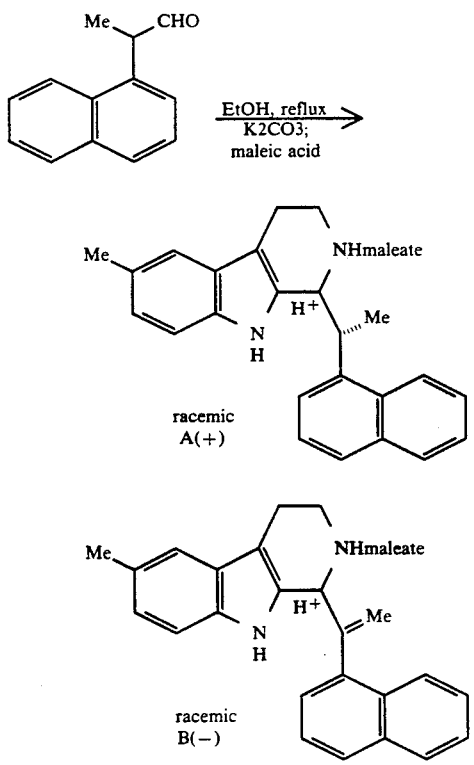

A solution of 5-methyltryptamine hydrochloride (1.11 g, 5.27 mmol) and 2-(1-naphthyl)propionaldehyde (0.97 g, 5.26 mmol) in 95% ethyl alcohol was heated to reflux for 48 hours under nitrogen atmosphere. The mixture was cooled to ambient temperature and concentrated under reduced pressure. The residue was partitioned between aqueous potassium carbonate solution and chloroform. The chloroform phase was dried over magnesium sulfate and concentrated under reduced pressure. The residue was subjected to flash chromatography on silica gel (25% methyl alcohol in chloroform as eluent), affording 529 mg of the higher rf isomer and 200 mg of the lower rf isomer. Each diastereomer, independently, was dissolved in ethyl acetate and treated with excess maleic acid. The maleate salts were isolated by filtration affording 570 mg of isomer A (+) and 30 mg of isomer B (+).

isomer A data: m/e=340.

| Analysis | Calculated | Found |
|---|---|---|
| C | 73.66 | 73.64 |
| H | 6.18 | 6.13 |
| N | 6.14 | 6.44 | isomer B data: m/e=340.

| Analysis | Calculated | Found |
|---|---|---|
| C | 73.66 | 73.41 |
| H | 6.18 | 6.04 |
| N | 6.14 | 5.89 |

EXAMPLE 4

Preparation of (+/−) 6-(1,1-dimethylethyl)-1-(1-naphthalenyl-1-ethyl)-1,2,3,4-tetrahydro-9H-pyrido[3,4-b]indole hydrochloride

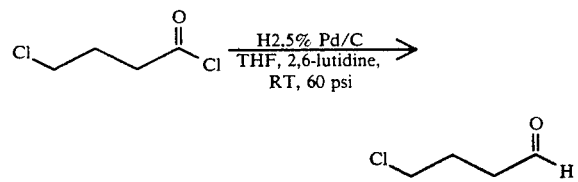

4-Chlorobutyryl chloride (300 g, 2.13 mol) was dissolved in dry THF (3 L). To this solution was added 2,6-lutidine (252 mL) followed by 5% Pd/C (30 g). This mixture was placed in a Parr hydrogenator and shaken under 60 psi of hydrogen for 6 hours. The mixture was purged with nitrogen, filtered, washing the catalyst with THF (500 mL), and concentrated at room temperature under reduced pressure. Distillation afforded 4-chlorobutanal (148.3 g) as a colorless liquid.

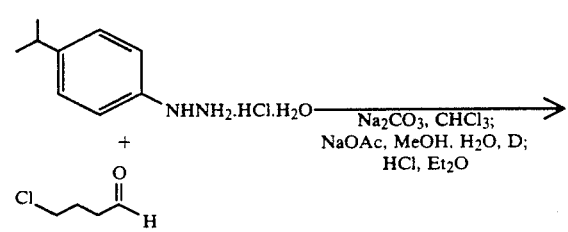

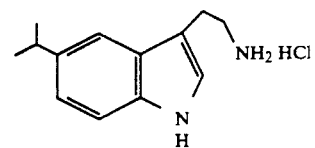

To a stirred suspension of 4-isopropyl-phenylhydrazine hydrochloride monohydrate (15.3 g, 91.95 mmol) in chloroform (250 mL) was added saturated sodium carbonate solution (250 mL). The mixture was stirred for 30 minutes until the organic phase appeared homogeneous, and extracted with chloroform (2×200 mL). The combined organic phases were concentrated to afford the hydrazine free base as a yellow oil. This oil was dissolved in methanol (200 mL) and water (5 mL) and treated with sodium acetate (6.72 g, 82 mmol) and 4-chlorobutanal (8.7 g, 82 mmol). The mixture was placed in a sealable tube and purged with nitrogen for 10 minutes. The tube was sealed and placed in an oil bath preheated to 100° C. Heating was continued for 18 hours. The resulting dark solution was cooled to ambient temperature and concentrated under reduced pressure. The residue was partitioned between chloroform/methanol (75/25 by volume) and aqueous sodium carbonate solution. The organic phase was concentrated and the crude indole ethanamine was purified by flash chromatography on silica gel (0–25% methanol gradient in chloroform as eluent). Fractions containing product were combined and concentrated. The oil was dissolved in diethyl ether (300 mL) containing 1% methanol and treated with dry HCl gas. The hydrochloride salt was isolated by filtration, washed with 2-propanol (50 mL) and diethyl ether (100 mL) and dried to afford 5-isopropyl-tryptamine hydrochloride (9.8 g) as a pale solid, which was used without further purification.

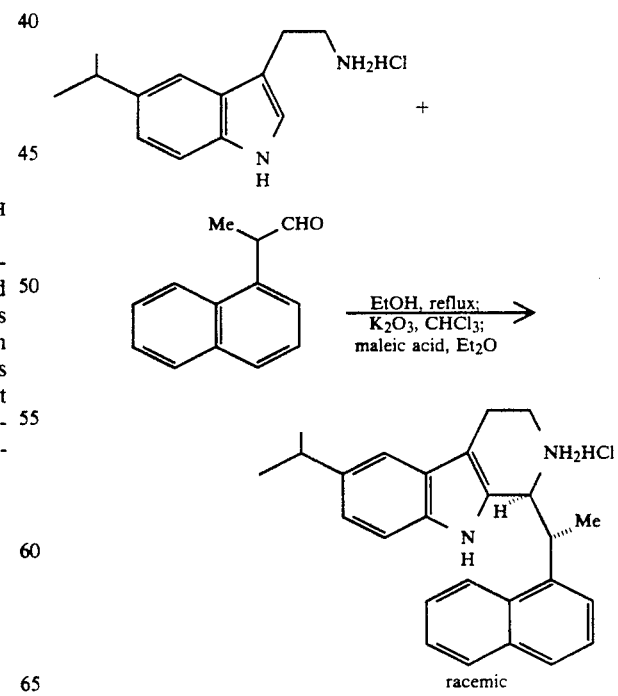

A solution of 5-isopropyltryptamine hydrochloride (1.24 g, 5.19 mmol) and 2-(1-naphthyl)propionaldehyde (0.95 g, 5.16 mmol) in 95% ethyl alcohol was heated to reflux for 48 hours under nitrogen atmosphere. The mixture was cooled to ambient temperature and concentrated under reduced pressure. The residue was partitioned between aqueous potassium carbonate solution and chloroform. The chloroform phase was dried over magnesium sulfate and concentrated under reduced pressure. The residue was subjected to flash chromatography on silica gel (25% methyl alcohol in chloroform as eluent), affording 500 mg of the higher rf isomer along with 400 mg of impure lower rf isomer. The major diastereomer was dissolved in ethyl acetate and treated with excess maleic acid. The hydrochloride salt was isolated by filtration affording 400 mg of named product as a pale solid.

m/e=369.

| Analysis | Calculated | Found |
|---|---|---|
| C | 74.36 | 74.58 |
| H | 6.66 | 6.64 |
| N | 5.78 | 5.81 |

EXAMPLE 5

Preparation of (+/−) 6-methyl-1-(1-naphthalenylmethyl)-1,2,3,4-tetrahydro-9H-pyrido[3,4-b]indole hydrochloride

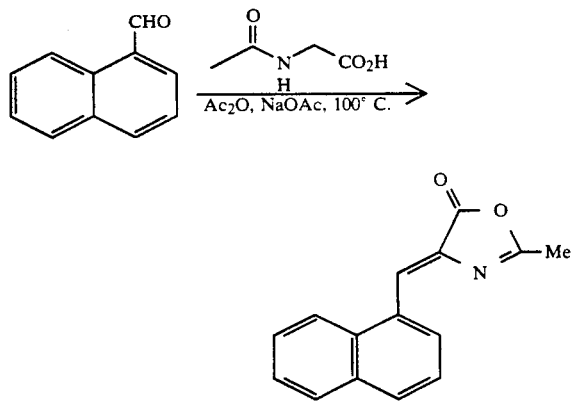

A solution of 1-naphthaldehyde (25.0 g, 0.16 mol), N-acetylglycine (19.0 g, 0.162 mol) and sodium acetate (13.1 g, 0.160 mol) in acetic anhydride (147 mL) was heated to 100° C. for 4 hours. The reaction mixture was cooled to ambient temperature poured onto ice (300 mL) with stirring. The product was isolated by filtration, washed with water (3×50 mL) and diethyl ether (3×50 mL) and dried under reduced pressure (11.82 g).

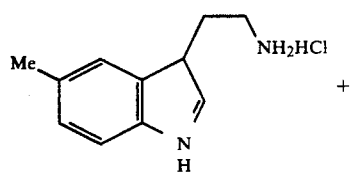

+

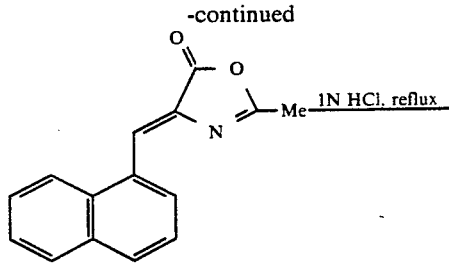

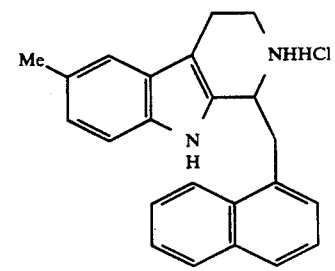

A suspension of azalactone prepared above (3.15 g, 13.3 mmol) and 5-methyltryptamine hydrochloride (2.0 g, 9.5 mmol) in 1N HCl (50 mL) was heated to reflux for 24 hours under nitrogen atmosphere. The reaction mixture was cooled to ambient temperature and the crude product isolated by filtration. The brown solid was triturated with isopropyl alcohol (3×50 mL) and washed with diethyl ether (3×50 mL). Recrystallization from ethanol afforded 1.94 g of desired product as the hydrochloride salt.

| Analysis | Calculated | Found |
|---|---|---|
| C | 76.12 | 76.03 |
| H | 6.39 | 6.22 |
| N | 7.72 | 7.52 |

EXAMPLE 6

Preparation of (+/−) 8-bromo-1-(1-naphthalenylmethyl)-1,2,3,4-tetrahydro-9H-pyrido[3,4-b]indole hydrochloride

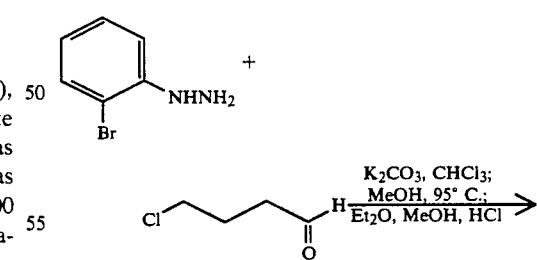

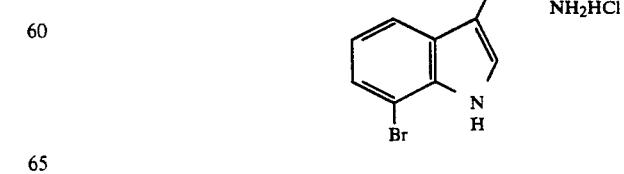

To a stirred suspension of 2-bromophenyl-hydrazine hydrochloride (25.8 g, 115 mmol) in chloroform (500 mL) was added saturated sodium carbonate solution (500 mL). The mixture was stirred for 30 minutes until the organic phase appeared homogenous, and extracted with chloroform (2×200 mL). The combined organic phases were concentrated to afford the hydrazine free base as a yellow oil. This oil was dissolved in methanol (100 mL) and treated slowly with 4-chlorobutanal (prepared as described in Example 4) (12.3 g, 115 mmol). The mixture was placed in a sealable tube and purged with nitrogen for 10 minutes. The tube was sealed and placed in an oil bath preheated to 95° C. Heating was continued for 18 hours. The resulting dark solution was cooled to ambient temperature and concentrated under reduced pressure. The residue was partitioned between chloroform/methanol (75/25 by volume) and aqueous sodium carbonate solution. The organic phase was concentrated and the crude indole ethanamine was purified by flash chromatography on silica gel (0–25% methanol gradient in chloroform as eluent). Fractions containing product were combined and concentrated. The oil was dissolved in diethyl ether (300 mL) containing 1% methanol and treated with dry HCl gas. The hydrochloride salt was isolated by filtration, washed with 2-propanol (50 mL) and diethyl ether (100 mL) and dried to afford 7-bromotryptamine hydrochloride (3.6 g) as a pale solid, which was used without further purification.

| Analysis | Calculated | Found |
|---|---|---|
| C | 61.77 | 61.48 |
| H | 4.71 | 4.63 |
| N | 6.55 | 6.73 |

EXAMPLE 7

Preparation of (+/−) 6-methyl-8-bromo-1-(1-naphthalenylmethyl)-1,2,3,4-tetrahydro-9H-pyrido[3,4-b]indole

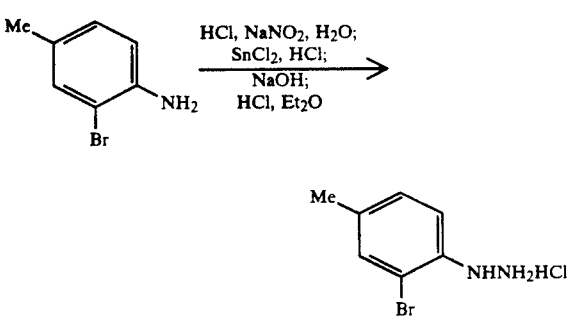

To a stirred, cooled (−5° C. solution of 2-bromo-4-methyl aniline (50.54 g, 0.272 mol) in concentrated HCl solution (200 mL) was added sodium nitrite (18.9 g, 0.274 mol) in water (200 mL) dropwise at such a rate as to maintain temperature below 5° C.. After complete addition, the mixture was further stirred at 5° C. for 30 minutes. A solution of tin chloride monohydrate (185.4 g, 0.822 mol) in concentrated HCl (total volume 400 mL) was added dropwise again maintaining temperature below 5° C.. After complete addition and 30 minutes of further stirring, the mixture was placed in the freezer overnight. The light brown solid which precipitated was isolated by filtration and washed with cold brine followed by a solution of petroleum ether/diethyl ether (2/1 by volume). This solid was slowly added to an ice cooled mixture of 50% sodium hydroxide solution/ethyl acetate. The mixture was extracted with ethyl acetate and the organic phase dried over magnesium sulfate. After filtration, the solution was concentrated to 400 mL total volume, diluted with diethyl ether (1.5 L) and treated with dry HCl. The product, 2-bromo-4-methyl-phenylhydrazine hydrochloride (52.4 g) was isolated as a light brown solid and used without further purification.

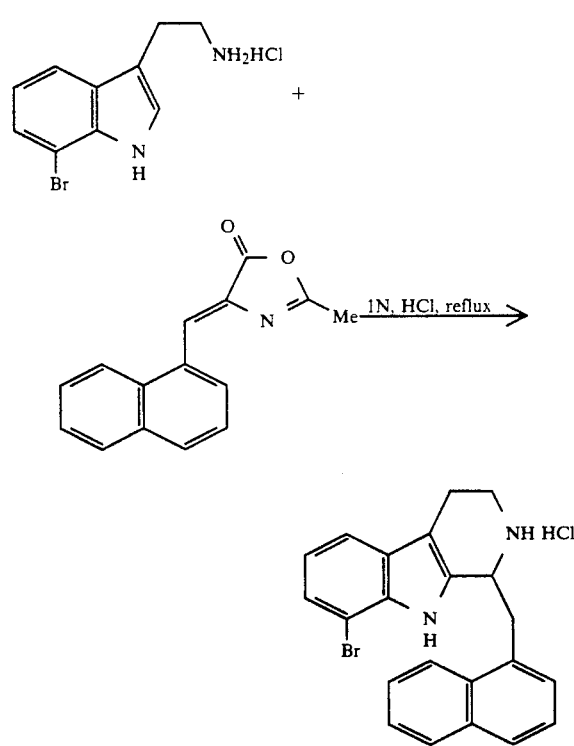

A suspension of azalactone (prepared as described in Example 5) (55 g, 6.53 mmol) and 7-bromotryptamine hydrochloride (1.50 g, 5.44 mmol) in 1N HCl (100 mL) was heated to reflux for 24 hours under nitrogen atmosphere. The reaction mixture was cooled to ambient temperature and the crude product isolated by filtration. The brown solid was triturated with isopropyl alcohol (3×50 mL) and washed with diethyl ether (3×50 mL). Recrystallization from ethanol afforded 260 mg of desired product as the hydrochloride salt. (mp=231°–233° C., dec.).

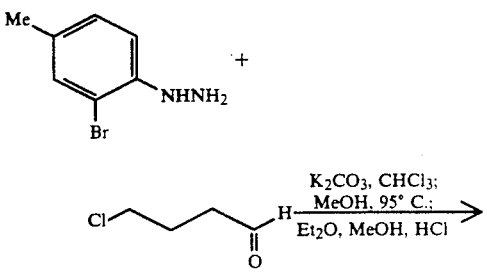

-continued

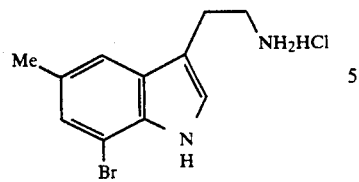

5-Methyl-7-bromotryptamine hydrochloride (4.95 g) was prepared as described in Example 6, except using 2-bromo-4-methylphenylhydrazine hydrochloride (21 g) as starting material.

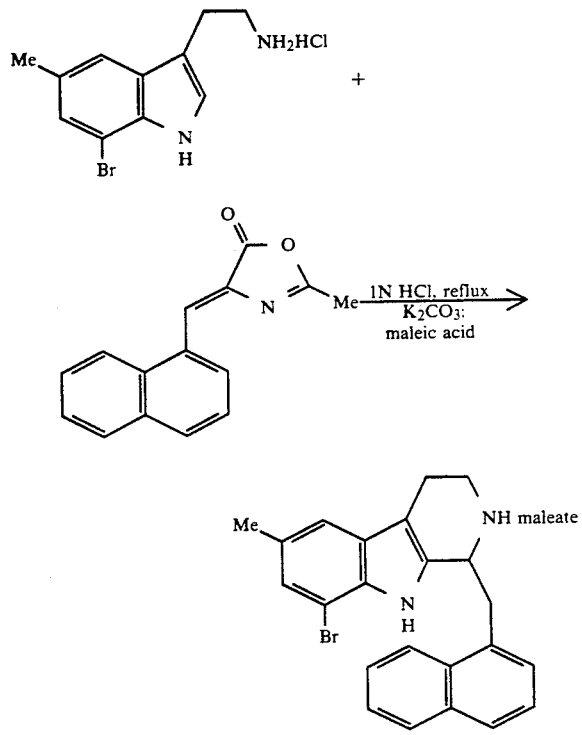

A suspension of azalactone (prepared as described in Example 5) (1.44 g, 6.07 mmol) and 5-methyl-7-bromotryptamine hydrochloride (1.12 g, 3.87 mmol) in 1N HCl (80 mL) was heated to reflux for 24 hours under nitrogen atmosphere. The reaction mixture was cooled to ambient temperature, neutralized with saturated aqueous potassium carbonate solution and extracted with chloroform. The solvent was removed under reduced pressure and the residue chromatographed on silica gel (ethyl acetate/0.2% NH4OH as eluent). The fractions containing product were pooled and concentrated under reduced pressure. The residue was dissolved in ethyl acetate containing 1% methanol and treated with maleic acid. The product was isolated as the maleate salt (840 mg) by filtration.
(mp=203°-205° C., dec.).

| Analysis | Calculated | Found |
|---|---|---|
| C | 62.20 | 62.44 |
| H | 4.83 | 5.07 |
| N | 5.37 | 5.56 |

EXAMPLE 8

Preparation of (+/−)-8-methoxy-1-(1-naphthalenylmethyl)-1,2,3,4-tetrahydro-9H-pyrido[3,4-b]indole

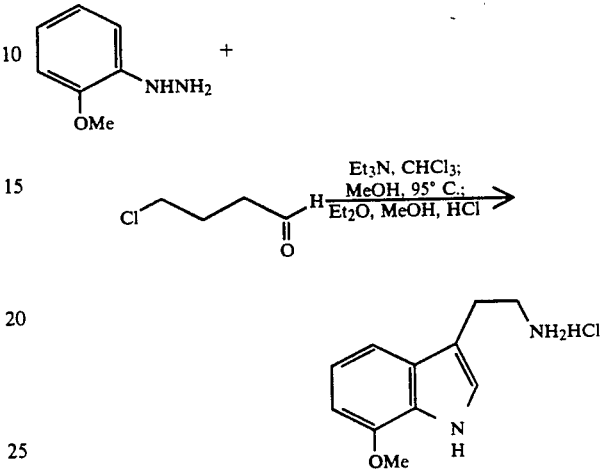

To a stirred, cooled (0° C.) suspension of 2-methoxyphenylhydrazine hydrochloride (14.44 g, 83 mmol) in THF (600 mL) was added 4-chlorobutanal prepared as described in Example 5 (9.0 g, 84 mmol) followed by dropwise addition of triethylamine (8.6 g, 85 mmol) in THF (20 mL). Upon complete addition, the cooling bath was removed and the solution stirred for 1 hour. The reaction mixture was filtered and the filter cake washed with THF (100 mL). The combined filtrates were concentrated to an orange oil, which was dissolved in methanol (150 mL) and water (5 mL). The solution was transferred to a sealable tube and purged with nitrogen for 10 minutes. The tube was sealed and placed in an oilbath preheated to 95° C. After heating for 14 hours, the reaction mixture was cooled to ambient temperature and concentrated under reduced pressure. The residue was partitioned between saturated aqueous potassium carbonate and 3:1 chloroform: 2-propanol. The organic phase was dried over sodium sulfate and concentrated. The residue was purified by flash chromatography on silica gel (15% methanol, 0.2% NH4OH, in chloroform as eluent). The fractions containing product were pooled and concentrated under reduced pressure. The residue was dissolved in methanol and treated with dry HCl and concentrated to afford 7-methoxytryptamine hydrochloride (4.04 g) as a stable foam, which was used without further purification.

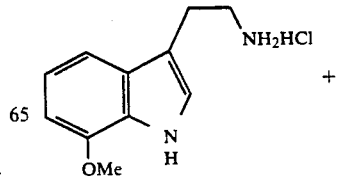

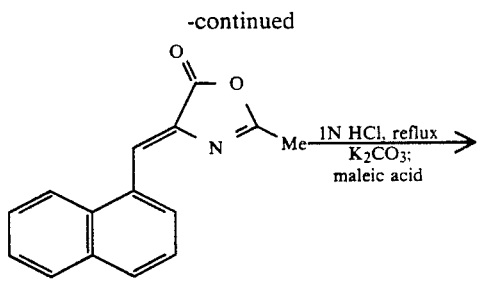

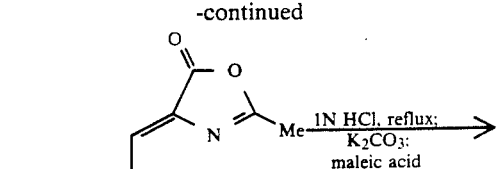

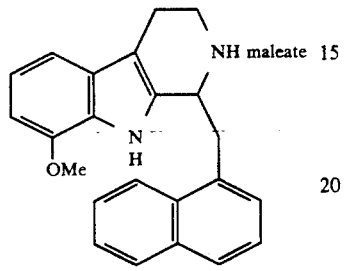

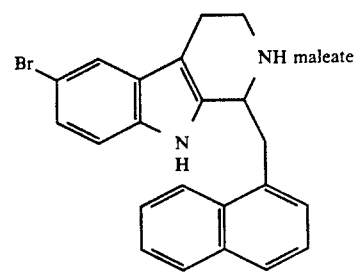

A suspension of azalactone (prepared as described in Example 5) (1.30 g, 5.5 mmol) and 7-methoxytryptamine hydrochloride (1.08 g, 4.8 mmol) in 1N HCl (100 mL) was heated to reflux for 24 hours under nitrogen atmosphere. The reaction mixture was cooled to ambient temperature, neutralized with saturated aqueous potassium carbonate solution and extracted with chloroform. The solvent was removed under reduced pressure and the residue chromatographed on silica gel (ethyl acetate/0.2% NH₄OH as eluent). The fractions containing product were pooled and concentrated under reduced pressure. The residue was dissolved in ethyl acetate containing 1% methanol and treated with maleic acid. The product was isolated as the maleate salt (880 mg) by filtration.

(mp=226°-227° C., dec.).

| Analysis | Calculated | Found |
|---|---|---|
| C | 70.73 | 70.61 |
| H | 5.72 | 5.77 |
| N | 6.11 | 6.03 |

EXAMPLE 9

Preparation of (+/−) 6-bromo-1-(1-naphthalenylmethyl)-1,2,3,4-tetrahydro-9H-pyrido[3,4-b]indole

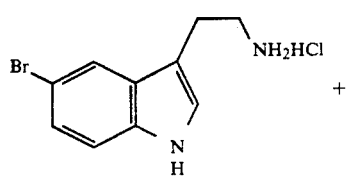

A suspension of azalactone (prepared as described in Example 5) (1.4 g, 5.9 mmol) and 5-bromotryptamine hydrochloride (1.77 g, 6.4 mmol) in 1N HCl (100 mL) was heated to reflux for 24 hours under nitrogen atmosphere. The reaction mixture was cooled to ambient temperature, neutralized with saturated aqueous potassium carbonate solution and extracted with chloroform. The solvent was removed under reduced pressure and the residue chromatographed on silica gel (ethyl acetate/0.2% NH₄OH as eluent). The fractions containing product were pooled and concentrated under reduced pressure. The residue was dissolved in ethyl acetate containing 1% methanol and treated with maleic acid. The product was isolated as the maleate salt (540 mg) by filtration.

(mp=234°-235° C., dec.).
m/e=390.

| Analysis | Calculated | Found |
|---|---|---|
| C | 61.55 | 61.38 |
| H | 4.57 | 4.64 |
| N | 5.52 | 5.29 |

EXAMPLE 10

Preparation of (+/−) 7-methyl-8-bromo-1-(1-naphthalenylmethyl)-1,2,3,4-tetrahydro-9H-pyrido[3,4-b]indole hydrochloride

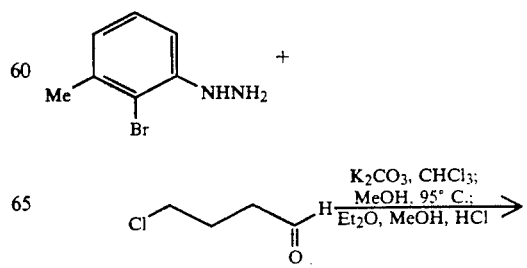

37
-continued

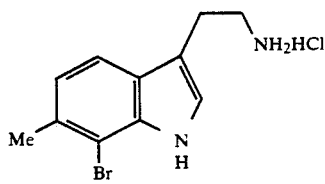

6-Methyl-7-bromotryptamine hydrochloride was prepared (2.42 g) as described for 5-methyl-7-bromotryptamine hydrochloride in Example 7, except using 2-bromo-3-methylphenylhydrazine hydrochloride as starting material.

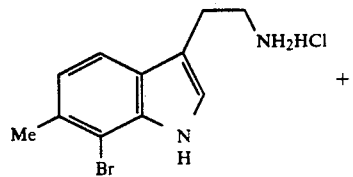

+

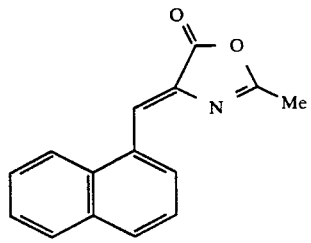

A suspension of azalactone (prepared as described in Example 5) (1.07 g, 4.51 mmol) and 6-methyl-7-bromotryptamine hydrochloride (1.22 g, 4.21 mmol) in 1N HCl (70 mL) was heated to reflux for 65 hours under nitrogen atmosphere. The reaction mixture was cooled to ambient temperature, neutralized with saturated aqueous potassium carbonate solution and extracted with chloroform. The solvent was removed under reduced pressure and the residue chromatographed on silica gel (ethyl acetate/0.2% NH₄OH as eluent). The fractions containing product were pooled and concentrated under reduced pressure. The residue was dissolved in ethyl acetate containing 1% methanol and treated with dry HCl. The product was isolated as the hydrochloride salt (840 mg) by filtration. (mp=276°–279° C., dec.).

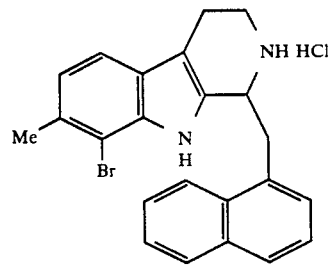

| Analysis | Calculated | Found |
|---|---|---|
| C | 62.53 | 62.79 |
| H | 5.02 | 4.96 |
| N | 6.34 | 6.19 |

38

EXAMPLE 11

Preparation of (+/−) 6-cyclohexyl-1-(1-naphthalenylmethyl)-1,2,3,4-tetrahydro-9H-pyrido[3,4-b]indole hydrochloride

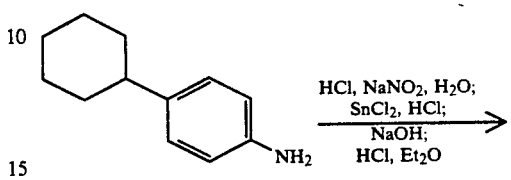

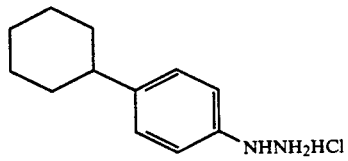

4-Cyclohexylphenylhydrazine hydrochloride (35.6 g) was prepared as described for 2-bromo-4-methylphenylhydrazine hydrochloride in Example 7, except using 4-cyclohexylaniline as starting material.

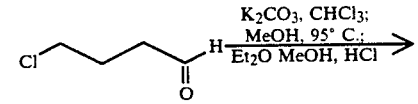

+

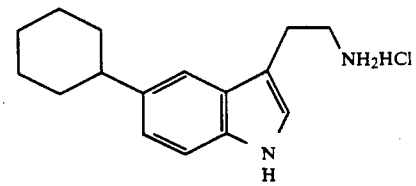

5-Cyclohexyltryptamine hydrochloride was prepared (1.29 g) as described for 5-methyl-7-bromotryptamine hydrochloride in Example 7, except using 4-cyclohexylphenylhydrazine hydrochloride as starting material.

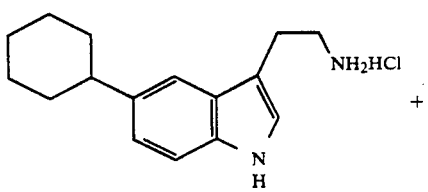

+

-continued

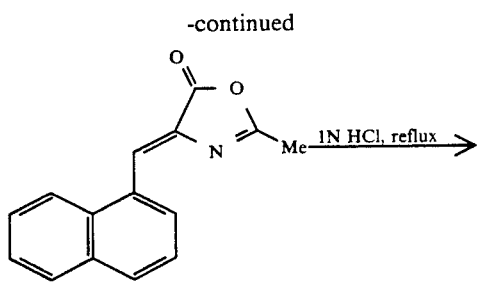

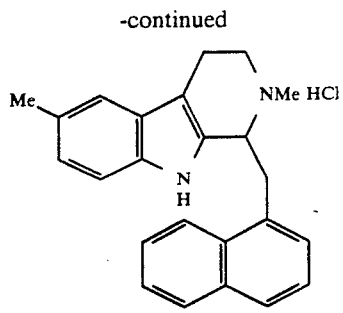

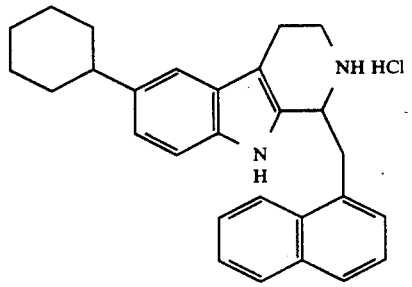

A suspension of azalactone (prepared as described in Example 5) (1.09 g, 4.59 mmol) and 5-cyclohexyltryptamine hydrochloride (1.28 g, 4.59 mmol) in 1N HCl (70 mL) was heated to reflux for 14 hours under nitrogen atmosphere. The reaction mixture was cooled to ambient temperature and the crude product isolated by filtration. The solid was recrystallized from ethanol (2X) to afford 690 mg of desired product as a pale solid hydrochloride salt.

m/e=395.

| Analysis | Calculated | Found |
|---|---|---|
| C | 78.03 | 78.26 |
| H | 7.25 | 7.06 |
| N | 6.50 | 6.48 |

EXAMPLE 12

Preparation of (+/−) 2,6-dimethyl-1-(1-naphthalenylmethyl)-1,2,3,4-tetrahydro-9H-pyrido[3,4-b]indole hydrochloride

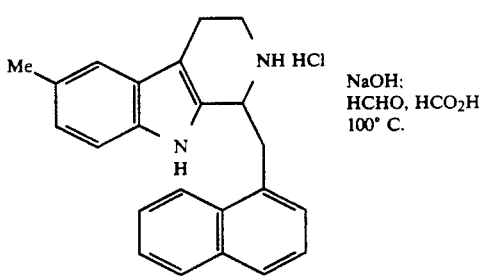

NaOH;
HCHO, HCO₂H
100° C.

To an aqueous solution (200 mL) of 5-methyl-1-(1-naphthalenylmethyl)-1,2,3,4-tetrahydro-9H-pyrido[3,4-b]indole hydrochloride (2.00 g, 5.51 mmol) previously prepared in Example 5, was added formic acid (4.1 mL) and formaldehyde solution (0.8 mL of 37% aqueous solution). The mixture was heated to reflux for 72 hours. The solution was made basic with saturated potassium carbonate solution and extracted with chloroform (2×100 mL). The combined organic phases were dried over potassium carbonate and concentrated under reduced pressure. The crude product was purified by flash chromatography on silica gel (chloroform as eluent). The fractions containing product were pooled and concentrated to a viscous oil. The oil was dissolved in diethyl ether and treated with anhydrous HCl and the resulting hydrochloride salt was isolated by filtration. Drying afforded the named product (1.34 g).

m/e=340.

| Analysis | Calculated | Found |
|---|---|---|
| C | 76.48 | 76.58 |
| H | 6.68 | 6.63 |
| N | 7.43 | 7.28 |

EXAMPLE 13

Preparation of (+/−) 5-fluoro-6-methyl-1-(1-naphthalenyl methyl)-1,2,3,4-tetrahydro-9H-pyrido[3,4-b]indole

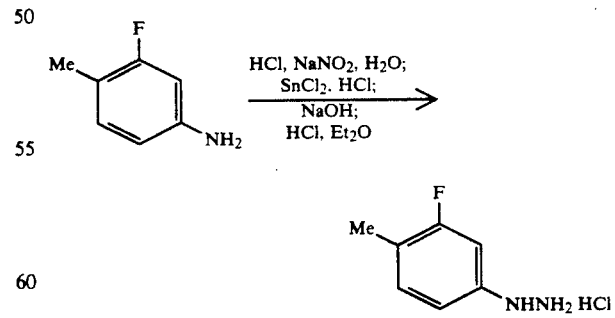

3-fluoro-4-methyl-phenylhydrazine hydrochloride (21.4 g -) was prepared as described for 2-bromo-4 methyl phenylhydrazine hydrochloride in Example 7, except using 3-fluoro-4-methylaniline as starting material.

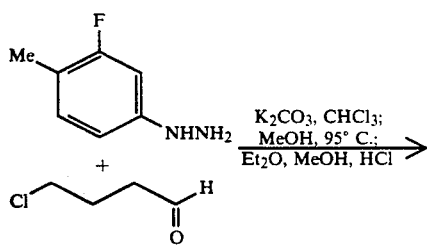

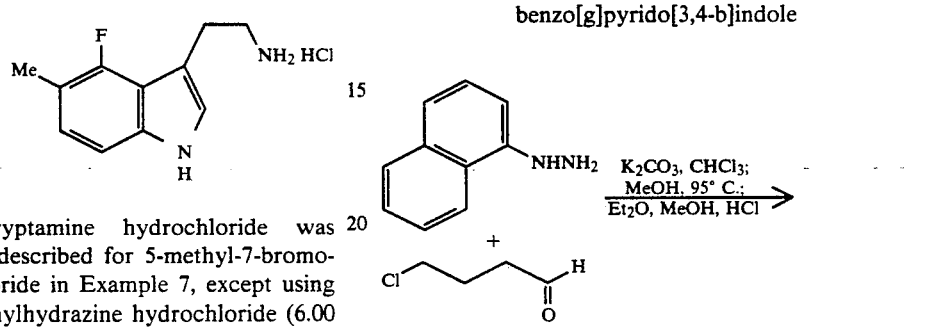

4-Fluoro-5-methyltryptamine hydrochloride was prepared (2.20 g) as described for 5-methyl-7-bromotryptamine hydrochloride in Example 7, except using 3-fluoro-4-methylphenylhydrazine hydrochloride (6.00 g) as starting material.

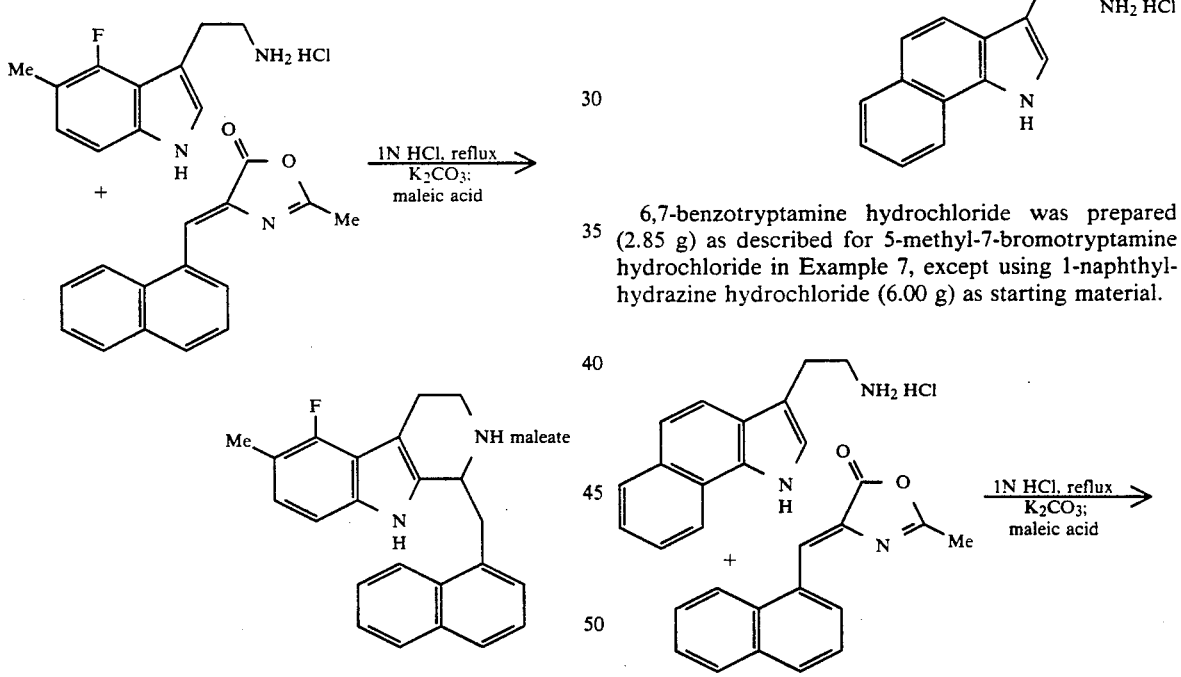

A suspension of azalactone (prepared as described in Example 5) (2.3 g, 9.6 mmol) and 4-fluoro-5-methyltryptamine hydrochloride (2.2 g, 9.6 mmol) in 1N HCl (40 mL was heated to reflux for 24 hours under nitrogen atmosphere. The reaction mixture was cooled to ambient temperature, neutralized with saturated aqueous potassium carbonate solution and extracted with chloroform. The solvent was removed under reduced pressure and the residue chromatographed on silica gel (ethyl acetate/0.2% NH₄OH as eluent). The fractions containing product were pooled and concentrated under reduced pressure. The residue was dissolved in ethyl acetate containing 1% methanol and treated with maleic acid. The product was isolated as the maleate salt (520 mg) by filtration.

| Analysis | Calculated | Found |
|---|---|---|
| C | 70.42 | 70.45 |
| H | 5.47 | 5.41 |
| N | 6.08 | 6.10 |

EXAMPLE 14

Preparation of (+/−) 7,8,9,10-tetrahydro-10-(1-naphthalenylmethyl)-11H-benzo[g]pyrido[3,4-b]indole

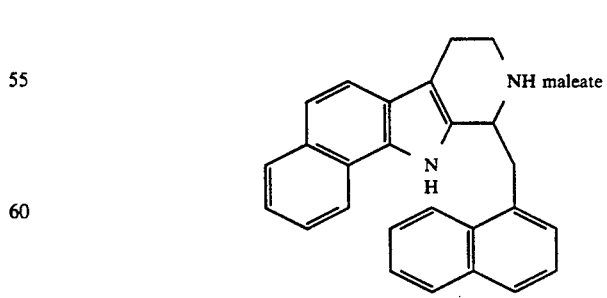

6,7-benzotryptamine hydrochloride was prepared (2.85 g) as described for 5-methyl-7-bromotryptamine hydrochloride in Example 7, except using 1-naphthylhydrazine hydrochloride (6.00 g) as starting material.

A suspension of azalactone (prepared as described in Example 5) (2.75 g, 11.6 mmol) and 6,7-benzotryptamine hydrochloride (2.85 g, 11.6 mmol) in 1N HCl (50 mL) was heated to reflux for 24 hours under nitrogen atmosphere. The reaction mixture was cooled to ambient temperature, neutralized with saturated aqueous potassium carbonate solution and extracted with chloroform. The solvent was removed under reduced pressure and the residue chromatographed on silica gel (ethyl acetate/0.2% NH4OH as eluent). The fractions containing product were pooled and concentrated under reduced pressure. The residue was dissolved in ethyl acetate containing 1% methanol and treated with maleic acid. The product was isolated as the maleate salt (300 mg) by filtration.

m/e=363.

| Analysis | Calculated | Found |
|----------|------------|-------|
| C | 75.30 | 75.04 |
| H | 5.48 | 5.36 |
| N | 5.85 | 5.76 |

EXAMPLE 15

Preparation of (+/−) 6-(1,1-dimethylethyl)-1,2,3,4-tetrahydro-1-(1-naphthalenylmethyl)-9H-pyrido[3,4b]indole

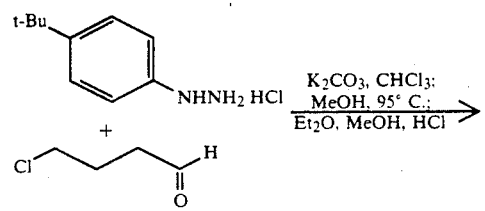

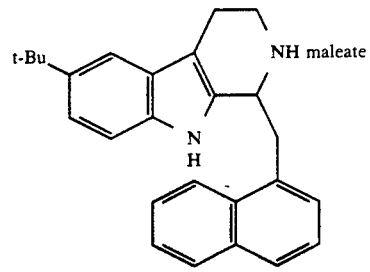

5-(1,1-dimethylethyl)-tryptamine hydrochloride was prepared (2.95 g) as described for 5-methyl-7-bromo-tryptamine hydrochloride in Example 7, except using 4-(1,1-dimethylethyl)phenylhydrazine hydrochloride (6.00 g) as starting material.

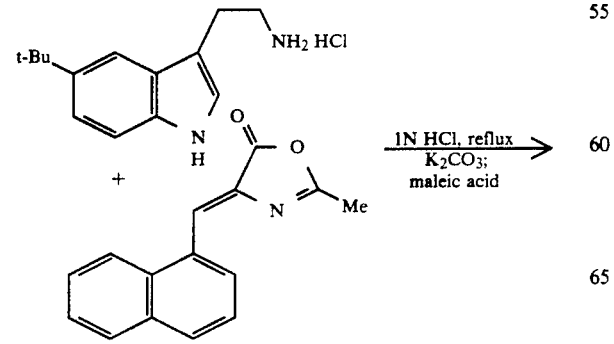

A suspension of azalactone (prepared as described in Example 5) (1.25 g, 5.26 mmol) and 5-(1,1-dimethylethyl)-tryptamine hydrochloride (1.33 g, 5.26 mmol) in 1N HCl (50 mL) was heated to reflux for 24 hours under nitrogen atmosphere. The reaction mixture was cooled to ambient temperature, neutralized with saturated aqueous potassium carbonate solution and extracted with chloroform. The solvent was removed under reduced pressure and the residue chromatographed on silica gel (ethyl acetate/0.2% NH4OH as eluent). The fractions containing product were pooled and concentrated under reduced pressure. The residue was dissolved in ethyl acetate containing 1% methanol and treated with maleic acid. The product was isolated as the maleate salt (700 mg) by filtration.

m/e=3

| Analysis | Calculated | Found |
|----------|------------|-------|
| C | 74.36 | 74.08 |
| H | 6.66 | 6.69 |
| N | 5.78 | 5.69 |

EXAMPLE 16

Preparation of (+/−) 6-(1-methylethyl)-1,2,3,4-tetrahydro-1-(1-naphthalenylmethyl)-9H-pyrido[3,4b]indole

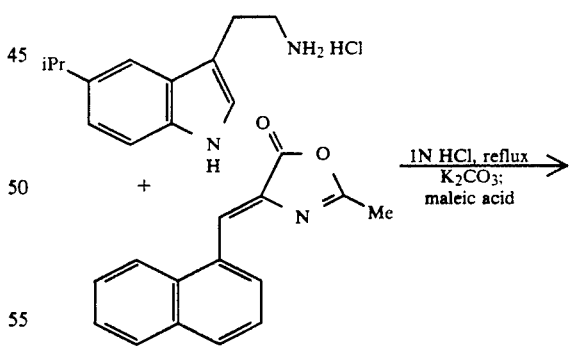

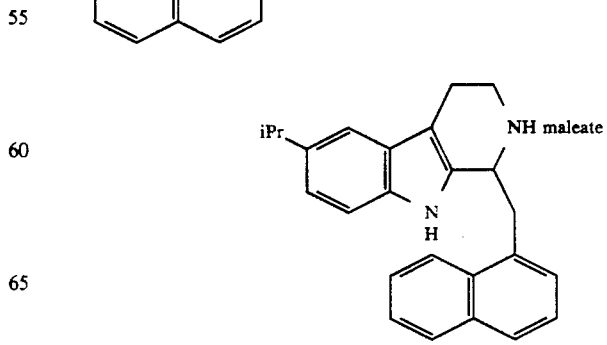

A suspension of azalactone (prepared as described in Example 5) (1.75 g, 7.38 mmol) and 5-isopropyltryptamine hydrochloride (prepared as described in Example 4) (1.76 g, 7.37 mmol) in 1N HCl (40 mL) was heated to reflux for 24 hours under nitrogen atmosphere. The reaction mixture was cooled to ambient temperature, neutralized with saturated aqueous potassium carbonate solution and extracted with chloroform. The solvent was removed under reduced pressure and the residue chromatographed on silica gel (ethyl acetate/0.2% NH4OH as eluent). The fractions containing product were pooled and concentrated under reduced pressure. The residue was dissolved in ethyl acetate containing 1% methanol and treated with maleic acid. The product was isolated as the maleate salt (671 mg) by filtration. m/e=355.

| Analysis | Calculated | Found |
|---|---|---|
| C | 74.02 | 74.08 |
| H | 6.43 | 6.21 |
| N | 5.95 | 5.83 |

EXAMPLE 17

Preparation of (+/−) 6,9-dimethyl-1,2,3,4-tetrahydro-1-(1-naphthalenylmethyl)-9H-pyrido[3,4-b]indole hydrochloride

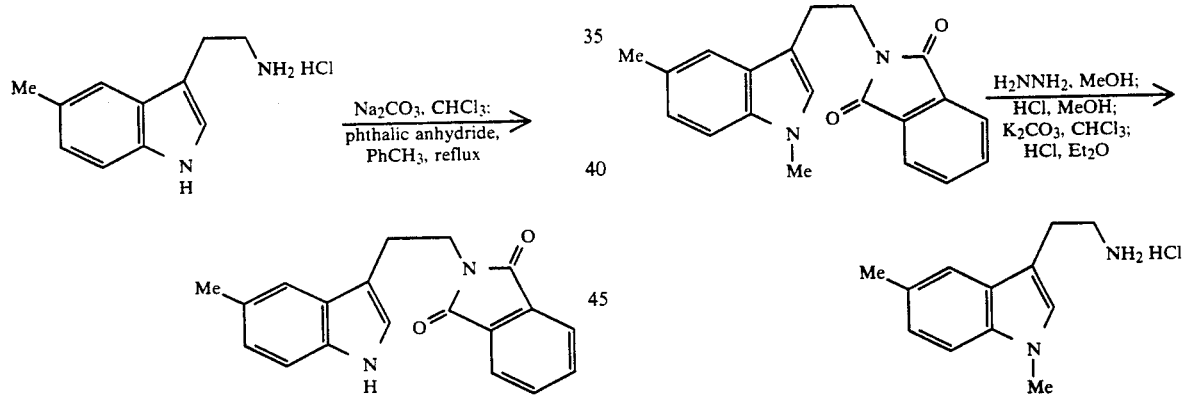

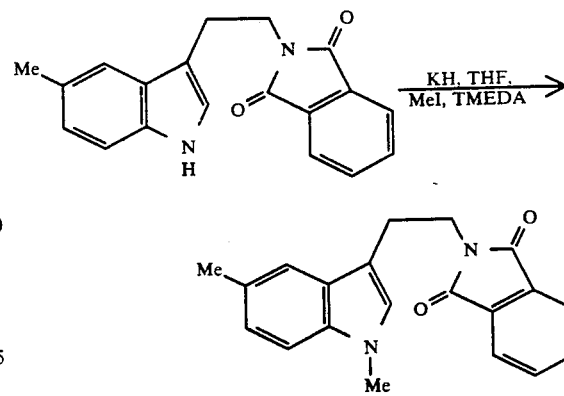

To a stirred suspension of 5-methyltryptamine hydrochloride (10.0 g, 43.2 mmol) in chloroform (300 mL) was added saturated sodium carbonate solution (300 mL). The mixture was stirred at ambient temperature for 1 hour. The layers were separated and the aqueous layer was back extracted with chloroform (2×100 mL). The combined organic layers were dried over sodium sulfate and concentrated. The residue was dissolved in toluene (300 mL) and treated with phthalic anhydride (7.05 g, 47.6 mmol). The solution was heated to reflux for 14 hours with azeotropic removal of water (by Dean-Stark trap). The solution was cooled to ambient temperature and concentrated to afford crude product as a pale foam. Recrystallization from ethanol afforded product phthalimide (13.52 g) as a white solid, which was used without further purification.

To a stirred, cooled (0° C.) suspension of potassium hydride (25% oil dispersion, 8.24 g, 51.3 mmol) in dry THF (50 mL) was added a solution of phthalimide prepared above (13.02 g, 42.8 mmol) int he THF (150 mL) over 30 minutes. After complete addition, the mixture was further stirred for 1 hour. Tetramethylethylenediaminde (7.7 mL, 51.3 mmol) was added, followed by methyl iodide (4.0 mL, 63.8 mmol). After 1 hour, the reaction was quenched by addition of water (200 mL), followed by extraction with diethyl ether (2×100 mL). The combined organic phases were dried over magnesium sulfate and concentrated under reduced pressure to afford product as a yellow solid (14 g) which was used without further purification.

A solution of phalimide prepared in the previous step (14 g, 42.8 mmol) in methanol (85 mL) was treated with hydrazine (3.4 mL, 109 mmol). The mixture was heated to reflux for 2 hours. The mixture was cooled to ambient temperature, treated with concentrated HCl (7 mL) and methanol (25 mL), and further heated to reflux for 14 hours. After cooling to ambient temperature, the mixture was partitioned between chloroform (200 mL) and saturated aqueous sodium carbonate solution (200 mL). The aqueous layer was further extracted with chloroform (2×100 mL) and the organic phases combined, dried over sodium sulfate and concentrated. The crude product was purified by flash chromatography on silica gel (0–25% methanol in chloroform/0.2% NH4OH as eluent). The product containing fractions were pooled and concentrated under reduced pressure. The residue was dissolved in diethyl ether and treated with anhydrous HCl. The product 1,5-dimethyltryptamine hydrochloride (6.08 g) was isolated by filtration as a tan solid and used without further purification.

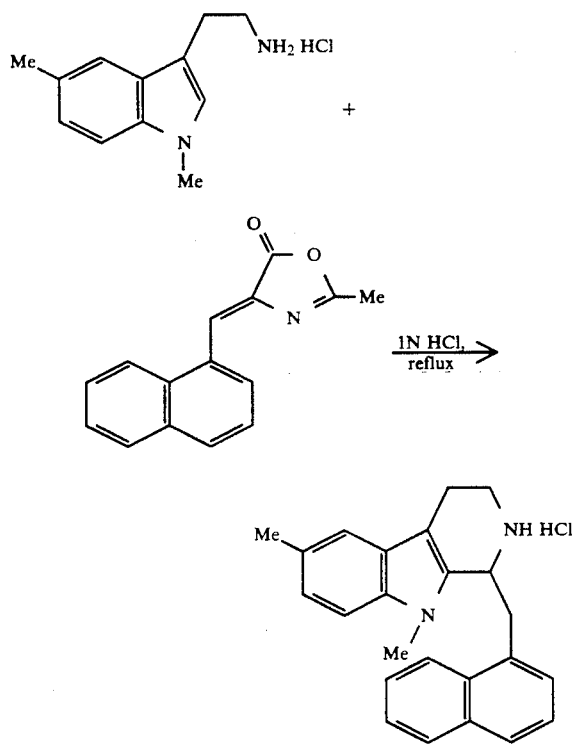

A suspension of azalactone prepared as described in Example 5 (1.06 g, 4.45 mmol) and 1,5-dimethyltryptamine hydrochloride (1.00 g, 4.47 mmol) in 1N HCl (50 mL) was heated to reflux for 48 hours under nitrogen atmosphere. The reaction mixture was cooled to ambient temperature and the crude product isolated by filtration. The brown solid was triturated with isopropyl alcohol (3×50 mL) and washed with diethyl ether (3×50 mL). Recrystallization from ethanol afforded 710 mg of desired product as the hydrochloride salt. m/e=340.

| Analysis | Calculated | Found |
|---|---|---|
| C | 76.48 | 76.78 |
| H | 6.68 | 6.58 |
| N | 7.43 | 7.50 |

EXAMPLE 18

Preparation of
(−)-(S)-6-methyl-1,2,3,4-tetrahydro-1-(1-naphthalenyl-methyl)-9H-pyrido[3,4-b]indole hydrochloride

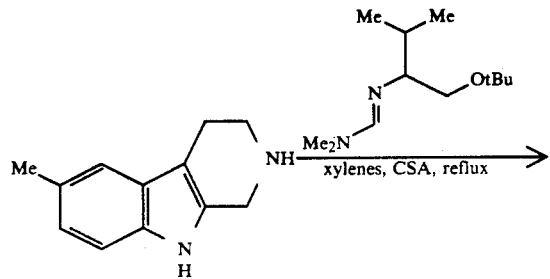

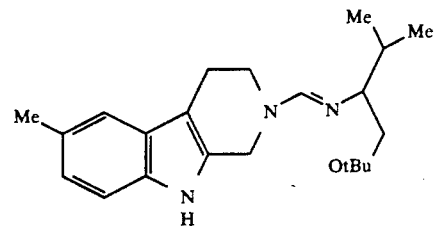

To a stirred solution of 6-methyl-1,2,3,4-tetrahydro-9H-pyrido[3,4-b]indole (3.14 g, 16.9 mmol) in dry xylenes (65 mL) was added (S)-N,N-dimethyl-N'-(1-tert-butoxy-3-methyl)-2-butylformamidine (3.79 g, 17.7 mmol) followed by camphorsulfonic acid (200 mg). The resulting solution was heated to reflux for 72 hours. The solution was cooled to ambient temperature and concentrated under reduced pressure. The residue was purified by flash chromatography on silica gel (1:3:6 triethylamine:ethyl acetate:hexanes as eluent). The product containing fractions were pooled and concentrated to afford the product formamidine (5.99 g) as a viscous oil which was used without further purification.

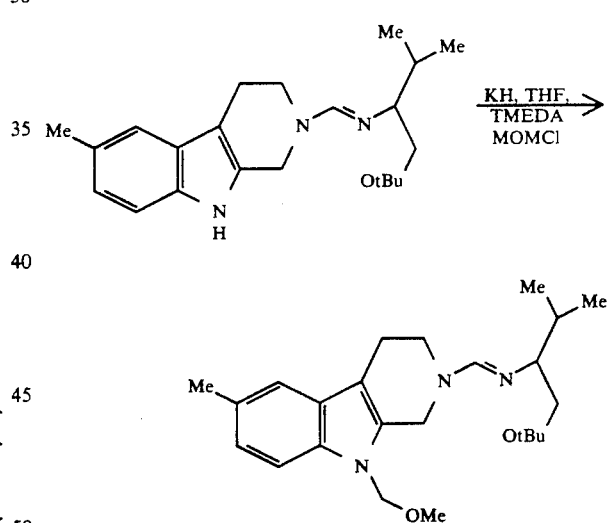

To a stirred, cooled (0° C.) suspension of potassium hydride (25% oil dispersion, 829 mg, 20.2 mmol) in THF (10 mL) was added formamidine prepared above (5.99 g, 16.8 mmol) in THF (45 mL). To this mixture was added tetramethylethylenediamine (3.0 mL, 20.2 mmol) followed by chloromethylmethyl ether (1.9 mL, 25.2 mmol). The mixture was stirred for an additional 1 hour and treated with water (50 mL). The mixture was partitioned between diethyl ether and water and the layers separated. The aqueous phase was extracted with diethyl ether (2×100 mL) and the organic phases combined, dried over potassium carbonate, and concentrated to afford product (6.73 g) as an orange oil, which was used without further purification.

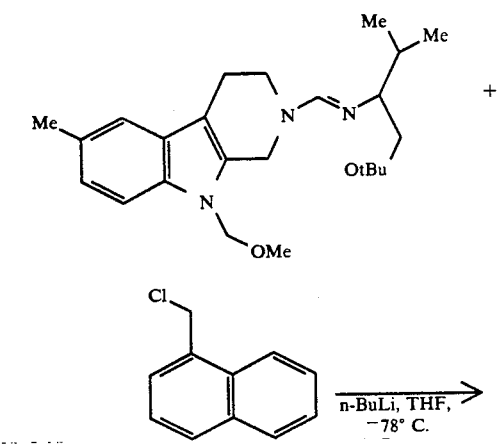

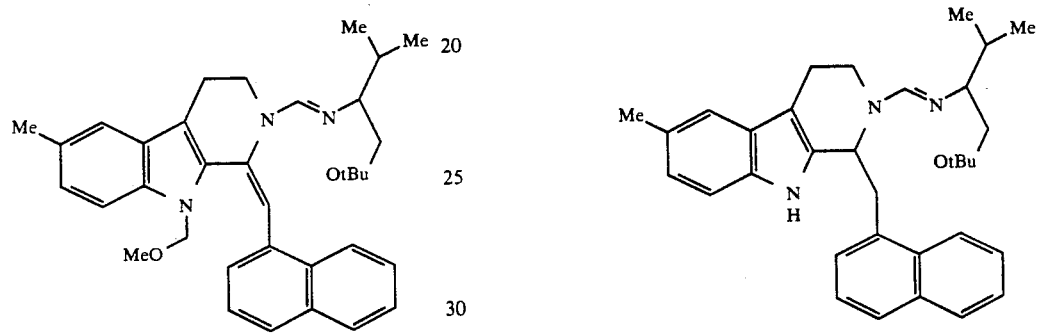

To a stirred, cooled (−78° C.) solution of previously prepared formamidine (3.36 g, 8.4 mmol) in dry THF (55 mL) was added n-BuLi (1.7M solution in hexanes, 5.4 mL, 9.18 mmol) dropwise over 5 minutes. The solution was further stirred at −78° C. solution for 1 hour and treated with 1-chloromethylnaphthalene (1.62 g, 9.18 mmol) in dry THF (10 mL). The solution was further stirred for 4 hours at −78° C. and allowed to warm to room temperature overnight. Wet THF was added (50 mL) and the solution was concentrated under reduced pressure. The residue was dissolved in chloroform and washed with water. The organic phase was dried over sodium carbonate and concentrated. The crude product was purified by flash chromatography on silica gel (1:3:6 triethylamine:ethyl acetate:hexanes as eluent). The product containing fractions were pooled and concentrated to afford product (3.48 g) as a viscous oil (m/e=539) which was used without further purification.

To a stirred solution of methoxymethyl indole prepared above (3.48 g , 6.45 mmol) in THF (30 mL) was added 2N HCl (30 mL). The mixture was stirred at ambient temperature for 24 hours, and partitioned between diethyl ether and water. The aqueous phase was back extracted with diethyl ether (2×50 mL) and the combined organic phases were washed with brine, dried over sodium carbonate, and concentrated under reduced pressure. The residue was dissolved in THF (20 mL) and treated with 2N sodium hydroxide solution (6 mL). After 2 hours, the reaction mixture was extracted with chloroform (2×100 mL). The organic phase was dried over sodium carbonate and concentrated to afford product (2.68 g) as a viscous oil.

(m/e=495 ).

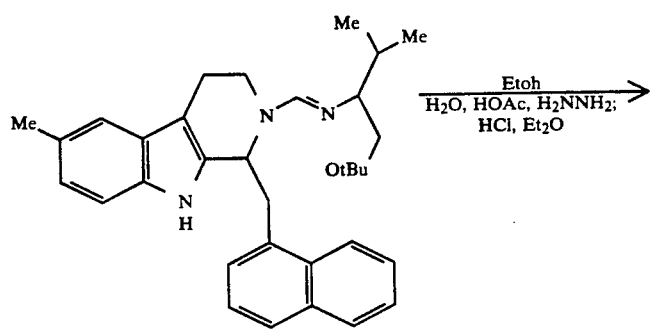

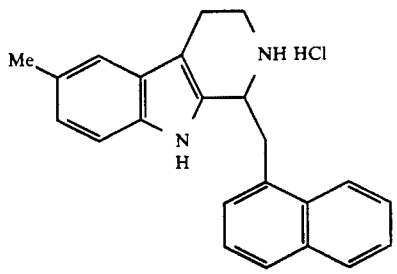

To a stirred, cooled (0° C.) solution of previously prepared formamidine (2.68 g, 5.41 mmol) in ethanol (100 mL) was added water (12 mL) followed by acetic acid (12 mL) and hydrazine hydrate (22 mL). The reaction vessel was placed in the freezer (−10° C.) for 72 hours. The mixture was warmed to ambient temperature and concentrated under reduced pressure. The crude product was dissolved in chloroform (300 mL) and washed with water (3×50 mL). The organic phase was dried over sodium carbonate and concentrated to a viscous oil. The oil was dissolved in diethyl ether and treated with anhydrous HCl. The hydrochloride salt (1.50 g) was isolated by filtration. Recrystallization from ethanol (2×) afforded material of constant rotation. Chiral HPLC confirmed enantiomeric purity as >95% ee.

(m/e=326).
specific rotation @589 nM = −40.21 (pyridine, C=1).
specific rotation @365 nM = +80.43 (pyridine, C=1).

| Analysis | Calculated | Found |
|---|---|---|
| C | 76.12 | 75.96 |
| H | 6.39 | 6.56 |
| N | 7.72 | 7.44 |

EXAMPLE 19

Preparation of 6-methyl-1-[(4-dimethylaminonaphthalenyl)methyl]1,2,3,4-tetrahydro-9H-pyrido[3,4-b]indole dihydrochloride.monohydrate

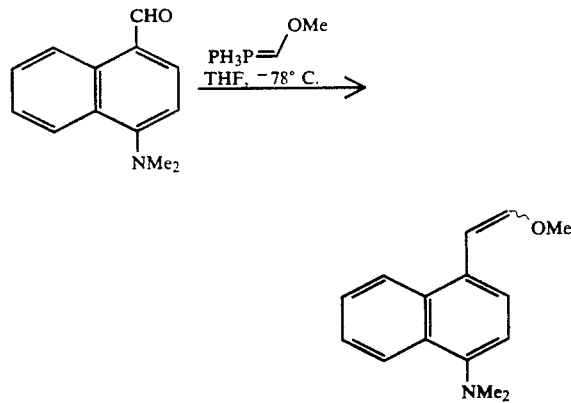

To a stirred, cooled (−78° C.) suspension of methoxymethyltriphenylphosphonium chloride (10.32 g, 30.1 mmol) in dry THF (150 mL) was added n-BuLi solution (18.8 mL. 1.6M, 30.1 mmol) dropwise by syringe. The orange suspension was stirred at −78° C. for 15 min. A solution of 4-dimethylamino-1-naphthaldehyde (5.00 g, 25.1 mmol) in THF (75 mL) was added to the ylide dropwise over 10 min. The reaction mixture was gradually warmed to ambient temperature and stirred 14H. Saturated ammonium chloride solution (100 mL) was added and the mixture extracted with diethyl ether (3×50 mL). The combined organic phases were dried over sodium sulfate and concentrated under reduced pressure. Chromatography on silica gel, eluting with 15% ethyl acetate/hexanes afforded product (5.43 g) as a mixture of olefin isomers which was used without further purification.

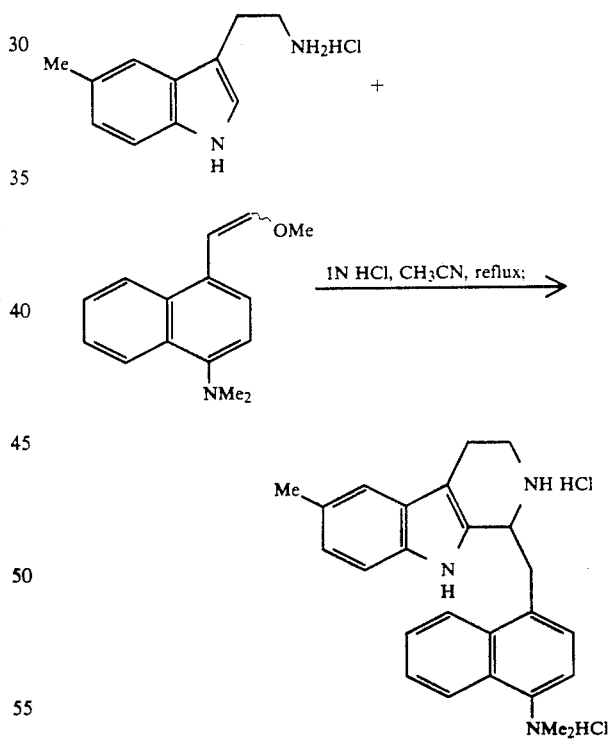

A mixture of 5-methyltryptamine hydrochloride (695 mg, 3.3 mmol) and 1-methoxy-4'-dimethylamino-benzostyrene (1.00 g, 4.4 mmol) in acetonitrile (20 mL) and 1N HCl solution (150 mL) was heated to reflux for 96H, with addition of 1 mL of conc HCl added at 4H. The reaction mixture was cooled to ambient temperature, neutralized with saturated aqueous potassium carbonate solution and extracted with chloroform. The combined organic phases were concentrated under reduced pressure and the residue chromatographed on silica gel (2.5% MeOH/chloroform/0.2% NH4OH as eluent).

The fractions containing product were pooled and concentrated under reduced pressure. The residue was dissolved in ethyl acetate and treated with anhydrous HCl. The product was isolated as the dihydrochloride salt monohydrate(1.22 g) by filtration.

mp. 231.3° C.

| Analysis | Calculated | Found |
|---|---|---|
| C | 65.21 | 65.30 |
| H | 6.79 | 6.60 |
| N | 9.13 | 9.03 |

As noted above, the compounds of the present invention are useful in blocking the effect of agonists at 5-$HT_{1c}$ receptors. Thus, the present invention also provides a method for blocking 5-$HT_{1c}$ receptors in mammals comprising administering to a mammal requiring blocking of a 5-$HT_{1c}$ receptor a receptor blocking dose of a compound of the invention.

The term "receptor blocking dose", as defined herein, means an amount of compound necessary to block a 5-$HT_{1c}$ receptor following administration to a mammal requiring blocking of a 5-$HT_{1c}$ receptor. The active compounds are effective over a wide dosage range. For example, dosages per day will normally fall within the range of about 0.05 to about 250 mg/kg of body weight. In the treatment of adult humans, the range of about 0.5 to 100 mg/kg, in single or divided doses, is preferred. However, it will be understood that the amount of the compound actually administered will be determined by a physician in light of the relevant circumstances, including the condition to be treated, the choice of compound to be administered, the age, weight, and response of the individual patient, the severity of the patient's symptoms, and the chosen route of administration, and therefore the above dosage ranges are not intended to limit the scope of the invention in any way. The compounds may be administered by a variety of routes such as oral, transdermal, subcutaneous, intranasal, intramuscular, and intravenous routes.

A variety of physiologic functions have been shown to be subject to be influenced by 5-$HT_{1c}$ receptors. Therefore, the compounds of the present invention can be used to treat a variety of disorders in mammals associated with these receptors. Such disorders include sleeping disorders, eating disorders, including bulimia and obesity, thermoregulation, sexual disorders, hyperactivity, excessive aggression, alcoholism, anxiety, obsessive-compulsive disorders, depression, panic disorders, Gilles de la Tourette syndrome, migraine headaches, and Alzheimer's Disease. Additionally, effects of the 5-$HT_{1c}$ receptor indicate that the compounds of the present invention can be useful for relieving the sensation of pain. Thus, the present invention also provides methods for treating the above disorders and for relieving the sensation of pain.

Several examples of more specific disorders which may be treated using compounds of this invention include, but are not limited to: (numerals in parenthesis refer to the DSM-III-R Classification Codes) Attention-deficit hyperactivity disorder (314.01), Conduct disorders (312.20, 312.00, 312.90), Primary degenerative dementia of the Alzheimer type, senile onset (290.30, 290.20, 290.21, 290.00), Primary degenerative dementia of the Alzheimer type, presenile onset (290.11, 290.12, 290.13, 290.10), Alcohol withdrawal delirium (291.00), Alcohol hallucinosis (291.30), Alcohol, dementia associated with alcoholism (291.20), cannabis, delusional disorder (292.11), cocaine, intoxication (305.60), hallucinogen, mood disorder (292.84), nicotine, withdrawal (292.00), phencyclidine or similarly acting arylcyclohexylamine, intoxication (305.90), other psychoactive substance, intoxication (305.90), delirium (293.00), dementia (294.10), Organic delusional disorder (293.81), organic hallucinosis (293.82), organic mood disorder (293.83), organic anxiety disorder (294.80), organic personality disorder (310.10), organic mental disorder (294.80), Schizophrenia, catatonic (295.21, 295.22, 295.23, 295.24, 295.25, 295.20), schizophrenia, disorganized (295.11, 295.12, 295.13, 295.14, 295.15, 295.00), schizophrenia, paranoid (295.31, 295.32, 295.33, 295.34, 295.35, 295.00), schizophrenia, undiffertiated (295.91, 295.92, 295.93, 295.94, 295.95, 295.00), schizophrenia, residual (295.61, 295.62, 295.63, 295.64, 295.65, 295.60), delusional (paranoid disorder (297.10), schizophreniform disorder (295.40), schizoaffective disorder (295.70), induced psychotic disorder (297.30), Bipolar disorder, mixed (296.61, 296.62, 296.63, 296.64, 296.65, 296.66, 296.60), bipolar disorder, manic (296.41, 296.42, 296.43, 296.44, 296.45, 296.46, 296.40), bipolar disorder, depressed (296.51, 296.52, 296.53, 296.54, 296.55, 296.56, 296.50), major depression, single episode (296.21, 296.22, 296.23, 296.24, 296.25, 296.26, 296.20), major depression, recurrent (296.31, 296.32, 296.33, 296.34, 296.35, 296.36, 296.30), obsessive compulsive disorder (300.30), post-traumatic stress disorder (309.89), generalized anxiety disorder (300.02), hypochondriasis (300.07), somatization disorder (300.81), male erectile disorder (302.72), intermittent explosive disorder (312.34), impulse control disorder (312.39), paranoid (301.00), schizoid (301.20), schizotypal (301.22), antisocial (301.70), and borderline (301.83).

One particularly unexpected embodiment of this invention provides selective ligands for the 5-$HT_{1c}$ receptor. Compounds with a high affinity for the 5-$HT_{1c}$ receptor generally are cross-reactive with the 5-$HT_2$ receptor as well. Now 5-$HT_{1c}$ receptors can be selectively modulated using compounds of this invention at rates set forth above for blocking the effects of agonists at 5-$HT_{1c}$ receptors. The selective affinity may provide treatments with fewer side effects and will facilitate the development of additional therapeutic agents.

The compounds of the present invention have been found to display excellent activity in a 5-$HT_{1c}$ receptor binding assay which measures the affinity of the compounds to bind to 5-$HT_{1c}$ receptors. Conversely, compounds with selective 5-$HT_{1c}$ activity displayed low affinity for the 5-$HT_2$ receptor. Therefore, the compounds were tested for 5-$HT_2$ affinity to demonstrate the selective 5-$HT_{1c}$ effect. The assays were conducted by the following procedures.

5-$HT_{1c}$ selective compounds can be identified using the following biological assay procedures. Compounds having a selective affinity for the 5-$HT_{1c}$ receptor have a low $IC_{50}$ in the 5-$HT_{1c}$ receptor assay and a higher $IC_{50}$ in the 5-$HT_2$ receptor assay. As shown by Table II (below) the compounds prepared in Examples 3, 4, 5, 7, 10, 13, 15, and 16 are particularly 5-$HT_{1c}$ selective.

I. Biological Reagent Preparation

Beef brain was removed immediately after slaughter, and choroid plexus were dissected over ice. Male Sprague-Dawley rats weighing 125–150 g (Harlan Industries, Cumberland, Ind.) were killed by decapitation.

The brain of each was immediately removed and the cerebral cortex was dissected over ice. Tissues were homogenized in 9 volumes of 0.32 mol/L sucrose and centrifuged at 1,000×g for 10 minutes. The supernatant was centrifuged at 17,000×g for 20 minutes. The pellet was suspended in 100 volumes of 50 mM Tris-HCL (pH7.4), incubated at 37° C. for 10 minutes and centrifuged at 50,000×g for 10 minutes, and the process was repeated three times. The final pellets were frozen at −70° C. and used within 2 weeks. Pellets were rehydrated with physiological buffer prior to use.

II. Assay Procedure

Radioligand binding assays for 5-HT$_{1c}$ and 5-HT$_2$ receptors were conducted according to described methods. The assays can be conducted as described by Hoyer D, Functional correlates of serotonin 5-HT$_{1c}$ recognition sites, *J. Receptor Res* 8, 59–81 (1988) and Hoyer D, Engel G, Kalkman HO Molecular pharmacology of 5-HT$_{1c}$ and 5-HT$_{1c}$ recognition sites in rat and pig brain membranes: Radioligand binding studies with [$^3$H]5-HT, [$^3$H]8-OH-DPAT, (−) [$^{125}$I]iodocyanopindolol, [$^3$H]mesulergine and [$^3$H]ketanserin, *Eur. J. Pharmacol.* 118, 13–23 (1985).

For 5-HT$_{1c}$ receptor assays increasing concentrations of experimental compound, 50 mM Tris HCl buffer pH [7.4], and tritiated mesulergine (2.0 nM) ($^3$H ligand) were combined in polystyrene tubes at room temperature. The reaction was initiated by the addition of the resuspended choroid plexus tissue which had been preincubated at 37° C. for 20 minutes. The reaction mixture was incubated in a 37° C. water bath for 15 minutes.

For 5-HT$_2$ receptor assays increasing concentrations of experimental compound, 50 mM Tris HCl buffer pH [7.4], and tritiated ketanserin (1 nM) ($^3$H ligand) were combined in polystyrene tubes at room temperature. The reaction was initiated by the addition of the resuspended rat cerebral cortex tissue which had been preincubated at 37° C. for 20 minutes. The reaction mixture was incubated in a 37° C. water bath for 30 minutes.

The above assays were modified after a number of compounds had been screened to accommodate the unexpectedly high potency of the compounds of this invention in the 5-HT$_{1c}$ assay. The concentration range of the experimental compound in the assays was changed from [0.1 to 1000 nM)] to [0.1 to 100 (nM)] to optimize the use of reagents and analysis time. The IC$_{50}$ values in Table II which are over 100 nM were accumulated before the modification of the concentration range of the experimental compound in the assay.

The reactions were terminated by rapid filtration, (Brandel Cell Harvestor), through Whatman GF/B glass filters that had been presoaked in Tris buffer pH [7.4]. The filters were then washed 2 times with 5 ml of ice cold Tris buffer pH [7.4]. Washed filters were placed in scintillation vials and 10 ml RedySolv, (Brandel), was added and samples were counted in a Searle D-300 beta counter. Means and standard error statistics were calculated for triplicate experimental determinations in certain cases. Mean values were obtained from three or more separate determinations. The incubation time for the reaction mixture was 15 minutes at 37° C.

Concentrations that caused a 50% inhibition of radioligand binding (IC$_{50}$) and Hill coefficient were obtained by computer-assisted regression analysis.

The results of the evaluation of certain compounds of the present invention in the 5-HT$_{1c}$ and 5-HT$_2$ binding assays are set forth below in Table II. In the Table, column 1 sets forth the Example Number of the compound evaluated, columns 2 and 3 are the IC$_{50}$ (nM) values for the 5-HT$_{1c}$ and 5-HT$_2$ receptors respectively.

TABLE II

| 5-HT Receptor Binding Displacement Assay | | |
|---|---|---|
| Example | 5-HT$_{1c}$ | 5-HT$_2$ |
| 1 | 6.4 | 56.1 |
| 2 | ** | ** |
| 3 | 6 | >100 |
| 4 | 14 | >100 |
| 5 | 30 | 267 |
| 6 | 13.2 | 40 |
| 7 | 60 | 247 |
| 8 | 63 | 65 |
| 9 | 27 | 87 |
| 10 | 44 | 142 |
| 11 | 189 | >100 |
| 12 | 54 | >100 |
| 13 | 16 | >100 |
| 14 | 61 | >100 |
| 15 | 11 | >100 |
| 16 | 9 | >100 |
| 17 | 23 | >100 |
| 18 | <100 | 108 |

While it is possible to administer a compound of the invention directly without any formulation, the compounds are preferably employed int he form of a pharmaceutical formulation comprising a pharmaceutically acceptable excipient and at least one compound of the invention. Such compositions contain from about 0.1 percent by weight to about 90.0 percent by weight of a present compound. As such, the present invention also provides pharmaceutical formulations comprising a compound of the invention and a pharmaceutically acceptable excipient therefor.

In making the compositions of the present invention, the active ingredient is usually mixed with an excipient which can be a carrier, or a diluent or be diluted by a carrier, or enclosed within a carrier which can be in the form of a capsule, sachet, paper or other container. When the carrier serves as a diluent, it can be a solid, semi-solid, or liquid material which acts as a vehicle, excipient, or medium for the active ingredient. Thus, the composition can be in the form of tablets, pills, powders, lozenges, sachets, cachets, elixirs, emulsions, solutions, syrups, suspensions, aerosols (as a solid or in a liquid medium), and soft and hard gelatin capsules.

The compounds of the invention may be delivered transdermally, if desired. Transdermal permeation enhancers and delivery systems, including patches and the like, are well known to the skilled artisan.

Examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

The compounds of this invention may be delivered transdermally using known transdermal delivery systems and excipients. Most preferably, a compound of this invention is admixed with permeation enhancers including, but not limited to, propylene glycol, polyethylene glycol monolaurate, and azacycloalkan-2-ones, and incorporated into a patch or similar delivery system. Additional excipients including gelling agents, emulsifiers, and buffers may be added to the transdermal formulation as desired.

For oral administration, a compound of this invention ideally can be admixed with carriers and diluents and molded into tablets or enclosed in gelatin capsules.

The compositions are preferably formulated in a unit dosage form, each dosage containing from about 0.1 to about 500 mg or more, usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect in association with a suitable pharmaceutical carrier.

In order to more fully illustrate the operation of this invention, the following formulation examples are provided. The examples are illustrative only, and are not intended to limit the scope of the invention. The formulations may employ as active compounds any of the compounds of the present invention.

Formulation 1

Hard gelatin capsules are prepared using the following ingredients:

|  | Amount Per Capsule | Concentration by Weight (percent) |
| --- | --- | --- |
| (+/−) 6-methyl-1-(1-(3-ethylamino naphthalenyl)-1-ethyl)-1,2,3,4-tetrahydro-9H-pyrido[3,4-b]indole (Z) 2-butenedioate | 250 mg | 55.0 |
| starch dried | 200 mg | 43.0 |
| magnesium stearate | 10 mg | 2.0 |
|  | 460 mg | 100.0 |

The above ingredients are mixed and filled into hard gelatin capsules in 460 mg quantities.

Formulation 2

Capsules each containing 20 mg of medicament are made as follows:

|  | Amount Per Capsule | Concentration by Weight (percent) |
| --- | --- | --- |
| 6-(1-methylethyl)-1,2,3,4-tetrahydro-1-(1-(4-dimethylaminonaphthalenyl)-methyl)-9H-pyrido[3,4b]indole (Z)-2-butenedioate | 20 mg | 10.0 |
| starch | 89 mg | 44.5 |
| microcrystalline cellulose | 89 mg | 44.5 |
| magnesium stearate | 2 mg | 1.0 |
|  | 200 mg | 100.0 mg |

The active ingredient, cellulose, starch, and magnesium stearate are blended, passed through a No. 45 mesh U.S. sieve and filled into a hard gelatin capsule.

Formulation 3

Capsules each containing 100 mg of medicament are made as follows:

|  | Amount Per Capsule | Concentration by Weight (percent) |
| --- | --- | --- |
| 5-fluoro-6-methyl-1-(1-(3-methylaminonaphthalenyl)-methyl)-1,2,3,4-tetrahydro-9H-pyrido-[3,4-b]indole (Z)-2-butenedioate | 100 mg | 30.00 |
| polyoxyethylene sorbitan monooleate | 50 mg | 0.02 |
| starch powder | 250 mg | 69.98 |
|  | 350.05 mg | 100.00 |

The above ingredients are thoroughly mixed and placed in an empty gelatin capsule.

Formulation 4

Tablets containing 10 mg of active ingredient are made as follows:

|  | Amount Per Capsule | Concentration by Weight (percent) |
| --- | --- | --- |
| 7,8,9,10-tetrahydro-10-(1-(2-dimethylaminonaphthyleneyl)-methyl)-11H-benzo[g]-pyrido[3,4-b]indole (Z)-2-butenedioate | 10 mg | 10.0 |
| starch | 45 mg | 45.0 |
| microcrystalline cellulose | 35 mg | 35.0 |
| polyvinylpyrrolidone (as 10% solution in water) | 4 mg | 4.0 |
| sodium carboxymethyl starch | 4.5 mg | 4.5 |
| magnesium stearate | 0.5 mg | 0.5 |
| talc | 1 mg | 1.0 |
|  | 100 mg | 100.0 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50°-60° C. and passed trough a No. 18 mesh U.S. sieve. The sodium carboxymethyl starch, magnesium stearate and talc, previously passed through a No. 60 mesh U.S. sieve, are then added to the granule which, after mixing, is compressed on a tablet machine to yield a tablet weighing 100 mg.

Formulation 5

A tablet formulation may be prepared using the ingredients below:

|  | Amount Per Capsule | Concentration by Weight (percent) |
| --- | --- | --- |
| 7-methyl-8-bromo-1-(1-cyclohexyleneyl-methyl)-1,2,3,4-tetrahydro-9H-pyrido-[3,4-b]indole | 250 mg | 38.0 |

|  | Amount Per Capsule | Concentration by Weight (percent) |
|---|---|---|
| hydrochloride microcrystalline cellulose | 400 mg | 60.0 |
| silicon dioxide fumed | 10 mg | 1.5 |
| stearic acid | 5 mg | 0.5 |
|  | 665 mg | 100.0 |

The components are blended and compressed to form tablets each weighing 665 mg.

Formulation 6

Suspensions each containing 5 mg of medicament per 5 ml dose are as follows:

|  | per 5 ml of suspension |
|---|---|
| 6-methyl-1-(1-(4-fluoronaphthalenyl)-methyl)-1,2,3,4-tetrahydro-9H-pyrido[3,4-b]indole hydrochloride | 5 mg |
| sodium carboxymethyl cellulose | 50 mg |
| syrup | 1.25 ml |
| benzoic acid solution | 0.10 ml |
| flavor | q.v. |
| color | q.v. |
| water | q.s. to 5 ml |

The medicament is passed through a No. 45 mesh U.S. sieve and mixed with the sodium carboxymethylcellulose and syrup to form a smooth paste. The benzoic acid solution, flavor and color is diluted with some of the water and added to the paste with stirring. Sufficient water is then added to produce the required volume.

Formulation 7

An aerosol solution is prepared containing the following components:

|  | Concentration by Weight (percent) |
|---|---|
| 5-methoxy-6-methyl-1-(1-naphthalenylmethyl)-1,2,3,4-tetrahydro-9H-pyrido[3,4-b]indole (Z)-2-butenedioate | 0.25 |
| ethanol | 29.75 |
| Propellant 22 (chlorodifluoromethane) | 70.00 |
|  | 100.00 |

The active compound is mixed with ethanol and the mixture added to a portion of the Propellant 22, cooled to $-30°$ C. and transferred to a filling device. The required amount is then fed to a stainless steel container and diluted further with the remaining amount of propellant. The valve units are then fitted to the container.

We claim:

1. A process for preparing a compound of formula (VI)

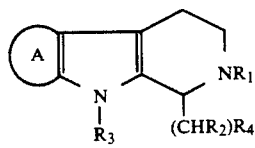

wherein:
$R_1$ is hydrogen or $C_1-C_3$ alkyl;
$R_2$ is hydrogen;
$R_3$ is hydrogen or $C_1-C_3$ alkyl;
$R_4$ is bicyclic or substituted bicyclic;
A is selected from the group consisting of

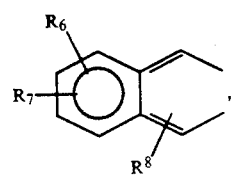

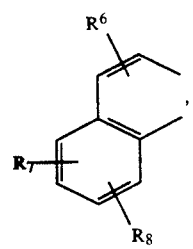

and

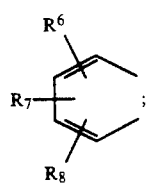

wherein
$R_6$ and $R_7$ are, independently, hydrogen, $C_1-C_6$ alkyl, $C_2-C_6$ alkenyl, halo, halo($C_1-C_6$)alkyl, halo($C_1-C_6$)alkenyl, $COR_5$, $C_1-C_{10}$ alkanoyl, $CO_2R_{5'}$, $(C_1-C_6)_m$ alkylamino, $NO_2$, $-SR_5$, or $OR_5$;
m is 1 or 2;
$R_5$ is independently hydrogen or $C_1-C_4$ alkyl;
$R_{5'}$ is $C_1-C_4$ alkyl;
$R_8$ is independently selected from the group consisting of an $R_6$ group, substituted $C_3-C_8$ cycloalkyl, $C_3-C_8$ cycloalkyl, $C_3-C_8$ cycloalkyl-($C_1-C_3$)alkyl, $C_5-C_8$ cycloalkenyl, substituted $C_5-C_8$ cycloalkenyl, $C_5-C_8$ cycloalkenyl-($C_1-C_3$)alkyl, $C_7-C_{16}$ arylalkyl; or
$R_6$ and $R_7$ together with the carbon atoms of group A form a 5- to 8-member carbon ring; or
a pharmaceutically acceptable salt or solvate thereof;
which process comprises contacting a compound of the formula (VII)

with a lactone of formula (VIII)

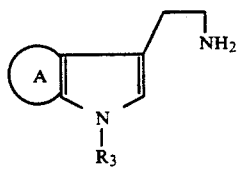
(VII)

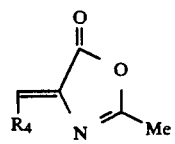
(VIII)

in the presence of a protic acid.

2. A process of claim 1 wherein the compound of formula VII is contacted with a lactone of formula VIII in an inert atmosphere.

3. A process of claim 2 wherein $R_1$ is hydrogen and $R_3$ is hydrogen or methyl.

4. A process of claim 3 wherein the protic acid is selected form the group consisting of hydrochloric acid, formic acid, perchloric acid, sulfuric acid, and phosphoric acid.

5. A process of claim 4 wherein the compound of formula VII is contacted with the lactone of formula VIII at the reflux temperature of the mixture.

6. A process of claim 5 wherein $R_4$ is naphthyl or substituted naphthyl.

* * * * *

UNITED STATES PATENT AND TRADEMARK OFFICE
CERTIFICATE OF CORRECTION

PATENT NO.     :  5,300,645

DATED          :  April 5, 1994

INVENTOR(S)    :  Audia, et al

It is certified that an error appears in the above-identified patent and that said Letters Patent is hereby corrected as shown below:

Column 1, line 19, delete the phrase "$5\text{-}HT_{1c}$" and insert therefore --$5\text{-}HT_2$--

Signed and Sealed this

Twenty-fifth Day of October, 1994

Attest:

BRUCE LEHMAN

*Attesting Officer*     *Commissioner of Patents and Trademarks*